US012729406B2

(12) United States Patent
Huepeden et al.

(10) Patent No.: US 12,729,406 B2
(45) Date of Patent: Sep. 8, 2026

(54) **OLIGONUCLEOTIDES FOR DETECTING *STAPHYLOCOCCUS***

(71) Applicant: BEIERSDORF AG, Hamburg (DE)

(72) Inventors: Jennifer Huepeden, Hamburg (DE); Heike Foelster, Hamburg (DE); Joern Hendrik Reuter, Henstedt-Ulzburg (DE); Charlotte Ahle, Hamburg (DE)

(73) Assignee: BEIERSDORF AG, Hamburg (DE)

(*) Notice: Subject to any disclaimer, the term of this patent is extended or adjusted under 35 U.S.C. 154(b) by 684 days.

(21) Appl. No.: 18/003,941

(22) PCT Filed: Jul. 6, 2021

(86) PCT No.: PCT/EP2021/068569

§ 371 (c)(1),
(2) Date: Dec. 30, 2022

(87) PCT Pub. No.: WO2022/008472

PCT Pub. Date: Jan. 13, 2022

(65) Prior Publication Data

US 2023/0257830 A1 Aug. 17, 2023

(30) Foreign Application Priority Data

Jul. 6, 2020 (EP) .................................... 20184339

(51) Int. Cl.
*C12Q 1/68* (2018.01)
*C12Q 1/689* (2018.01)

(52) U.S. Cl.
CPC ....... *C12Q 1/689* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 8,632,968 | B2 | 1/2014 | Perera et al. | |
| 9,434,999 | B1 * | 9/2016 | Ao ....................... | C12Q 1/6848 |
| 2010/0204266 | A1 | 8/2010 | Ecker et al. | |
| 2011/0312504 | A1 | 12/2011 | Driebe et al. | |
| 2017/0349937 | A1 | 12/2017 | Savelkoul | |

FOREIGN PATENT DOCUMENTS

| | | | |
|---|---|---|---|
| WO | 2008118809 | A1 | 10/2008 |
| WO | 2011116313 | A1 | 9/2011 |

OTHER PUBLICATIONS

Heikens et al. (Journal of Clinical Microbiology, May 2005, p. 2286-2290) (Year: 2005).*

Drinka et al. (Journal of the American Medical Directors Association. vol. 13, Issue 1, Jan. 2012, pp. 75-79) (Year: 2012).*

Gulilat et al. (BMC Medical Genomics (2019) 12:81; 17 pages) (Year: 2019).*

Van Reckem et al. (Microorganisms 2020, 8, 897; doi:10.3390/microorganisms8060897) (Year: 2020).*

Martineau et al. (Journal of Clinical Microbiology, Jul. 2001, p. 2541-2547) (Year: 2001).*

Hwang Journal of Clinical Microbiology, Dec. 2011, p. 4142-4149 (Year: 2011).*

Holger Brüggemann et al., "*Staphylococcus saccharolyticus* Isolated From Blood Cultures and Prosthetic Joint Infections Exhibits Excessive Genome Decay", Frontiers in Microbiology, Lausanne, (Mar. 12, 2019), vol. 10, doi:10.3389/fmicb.2019.00478, ISSN 1664-302X.

Charlotte M. Ahle et al., "*Staphylococcus saccharolyticus:* An Overlooked Human Skin Colonizer", Microorganisms, (Aug. 1, 2020), vol. 8, No. 8, doi:10.3390/microorganisms8081105, ISSN 2076-2607, p. 1105.

Bieber et al., "*Staphylococcus lugdunensis* in several niches of the normal skin flora", Clinical Microbiology and Infection, vol. 16 No. 4, Apr. 2010.

Bolyer et al., "Reproducible, interactive, scalable and extensible microbiome data science using QIIME 2", Nature Biotechnology, vol. Aug. 2, 37019, pp. 848-857.

Callahan et al., "DADA2: High-resolution sample inference from Illumina amplicon data", Nature Methods, vol. 13 No. 7, Jul. 2016 581.

Dickson et al., "Analysis of Culture-Dependent versus Culture-Independent Techniques for Identification of Bacteria in Clinically Obtained Bronchoalveolar Lavage Fluid", Journal of Clinical Microbiology, Oct. 2014 vol. 52 No. 10, pp. 3605-3613.

Everveen et al., "A generic workflow for Single Locus Sequence Typing (SLST) design and subspecies characterization of microbiota", Scientific Reports (2019) 9:19834 https://doi.org/10.1038/s41598-019-56065-y.

Evans et al., "Individual Differences in the Bacterial FLora of the Skin of the Forehead: Pepticoccus Saccharolyticus", Journal of Investigative Dermatology, vol. 71, No. 3, pp. 152-153, 1978.

Evans et al., "Isolation and Identification of Pepticoccus Saccharolyticus from Human Skin", Journal of Clinical Microbiology, Mar. 1978, pp. 261-264.

Fan et al., "MpsAB is important for *Staphylococcus aureus* virulence and growth at atmospheric CO2 levels", Nature Communications (2019) 10:3627 https://doi.org/10.1038/s41467-019-11547-5.

(Continued)

*Primary Examiner* — Juliet C Switzer
(74) *Attorney, Agent, or Firm* — Abel Schillinger, LLP

(57) ABSTRACT

The present invention relates to the field of nucleic acid amplification. More particularly, the invention relates to oligonucleotide primers for amplifying the sequence or part of the sequence of a *Staphylococcus tuf* gene. In another aspect, the invention relates to a method for identifying one or more *Staphylococcus* species and/or strains which are present in a biological sample, such as a skin swab. In yet another aspect, the invention relates to the use of an oligonucleotide primer of the present invention for amplifying the sequence or part of the sequence of a *Staphylococcus tuf* gene. Kits which comprise an oligonucleotide primer of the present invention are also provided for carrying out the methods of the invention.

12 Claims, 5 Drawing Sheets

Specification includes a Sequence Listing.

(56) References Cited

OTHER PUBLICATIONS

Foster, "Staphylococcal skin disease in livestock", Vet Dermatol 2012; 23: 342-e63.
Grice et al., "Topographical and Temporal Diversity of the Human Skin Microbiome", Science 34, vol. 324, May 29, 2009, pp. 1190-1192.
Hazarika et al., "Cutaneous infection associated with *Staphylococcus hyicus* in cattle", Research in Veterinary Science 1991, 50, pp. 374-375.
Kloos et al., "Distribution and Persistence of *Staphylococcus* and Micrococcus Species and Other Aerobic Bacteria on Human Skin", Applied Microbiology, vol. 30, No. 3, Sep. 1975, pp. 381-395.
Kloos et al., "*Staphylococcus auricularis* sp. nov. : an Inhabitant of the Human External Ear", International Journal of Systematic Bacteriology, vol. 33, No. 1, Jan. 1983, pp. 9-14.
Kong et al., "Skin Microbiome: Looking Back to Move Forward", Journal of Investigative Dermatology (2012) 132, pp. 933-939.
Mansson et al., "Genomic relatedness of *Staphylococcus pettenkoferi* isolates of different origins", Journal of Medical Microbiology 2017 66:601-608.
Martineau et al., "Development of a PCR Assay for Identification of *Staphylococciat* Genus and Species Levels", Journal of Clinical Microbiology, vol. 39, No. 7, Jul. 2001, pp. 2541-2547.
Meugnier et al., "Identification and ribotyping of *Staphylococcus xylosus* and *Staphylococcus equorum* strains isolated from goat milk and cheese", International Journal of Food Microbiology 31 (1996), pp. 325-331.
Oh et al., "Biogeography and individuality shape function in the human skin metagenome", Nature vol. 514, Oct. 2, 2014. pp. 59-77.
Oh et al., "Temporal Stability of the Human Skin Microbiome", Cell 165, pp. 854-866, May 5, 2016.
Pallen et al., "Bacterial pathogenomics", Nature vol. 449, Oct. 18, 2007, pp. 835-842.
Schleifer et al., "Isolation and Characterization of Staphylococci from Human Skin", International Journal of Systematic Bacteriology Jan. 1975, pp. 50-61.
Steinbrueckner et al., "Facing a mysterious hospital outbreak of bacteraemia due to *Staphylococcus saccharolyticus*", doi: 10.1053/jhin.2001.1105, available online at http://www.idealibrary.com on IDEAL.
Strube et al., "A detailed investigation of the porcine skin and nose microbiome using universal and *Staphylococcus specific* primer", Scientific Reports (2018) 8:12751.
Warnes et al., "Package 'gplots'", Various Programming Tools for Plotting Data 2020.
Wickham, "ggplot 2: Elegant Graphics for Data Analysis", Springer Verlag New York 2009.
Zong, "The newly-recognized species *Staphylococcus massiliensis* is likely to be part of the human skin microflora", Antonie van Leeuwenhoek (2012) 101:449-451.

* cited by examiner tuf2_miseq_F (SEQ ID NO:1)
5'-ACAGGCCGTGTTGAACGTG-3' tuf2_miseq_R (SEQ ID NO:2)
5'-ACAGTACGTCCACCTTCACG-3' tuf2_miseq_F (SEQ ID NO:3)
5'-TCGTCGGCAGCGTCAGATGTGTATAAGAGACAGACAGGCCGTGTTGAACGTG-3' tuf2_miseq_R (SEQ ID NO:4)
5'-GTCTCGTGGGCTCGGAGATGTGTATAAGAGACAGACAGTACGTCCACCTTCACG-3'

B
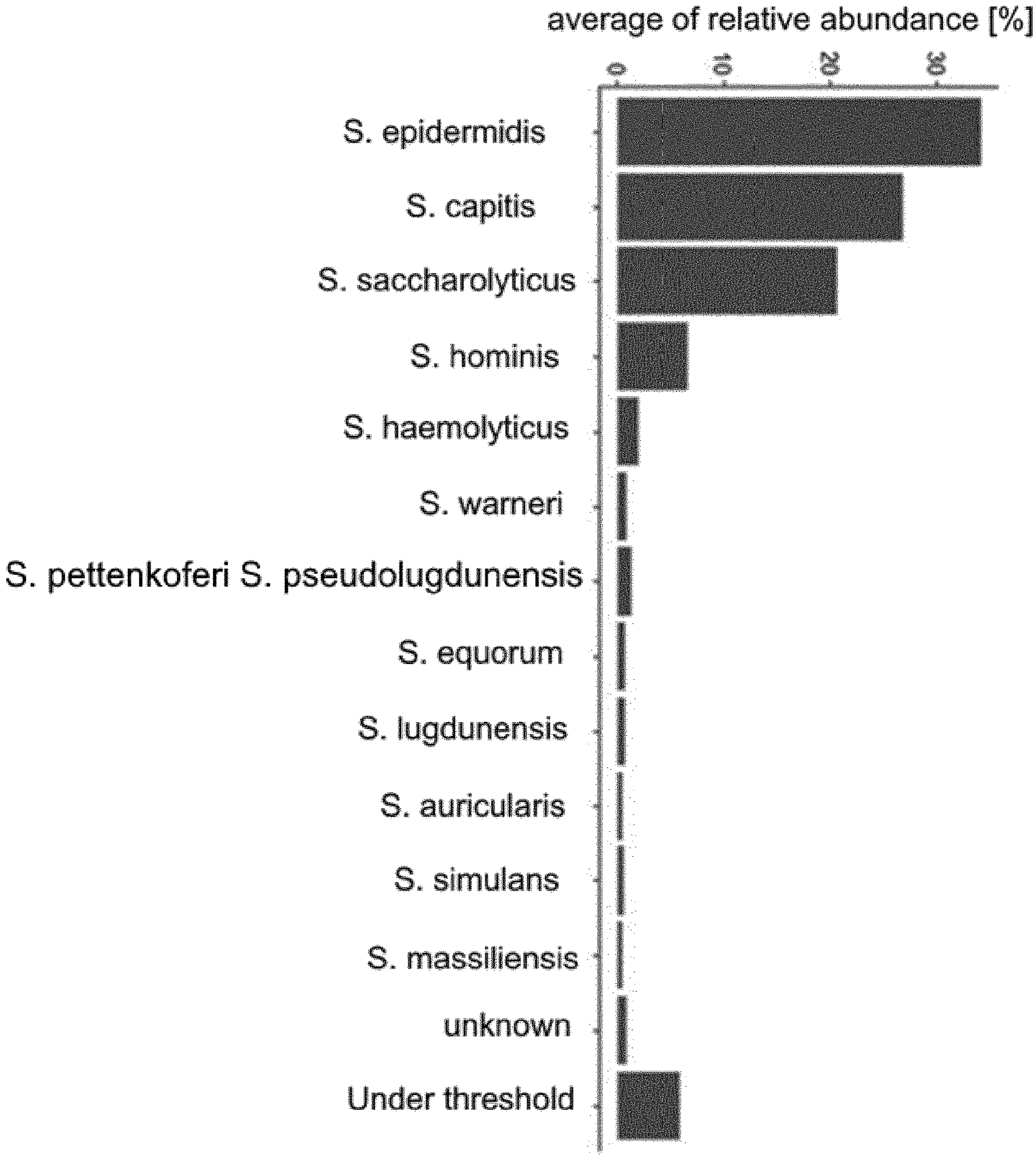
FIG. 2B – continued

C
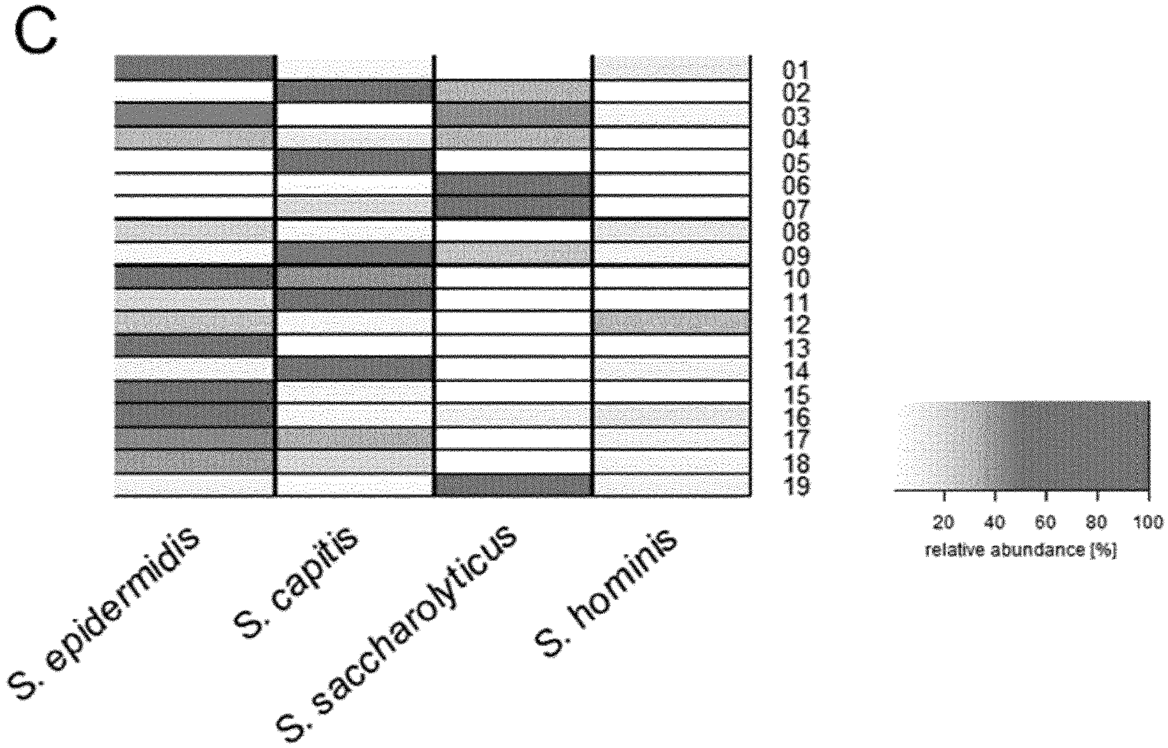
FIG. 2C - continued rpsk forw (SEQ ID NO:101)
5'- TGGCACGTAAACAAGTATC -3' rpsk rev (SEQ ID NO:102)
5'- GACGACGTTTTGGTGGAC -3' tuf-alt forw (SEQ ID NO:103)
5'- GGCCGTGTTGAACGTGGTCAAATC -3' tuf-alt rev (SEQ ID NO:104)
5'-TIACCATTTCAGTACCTTCTGGTAA -3'

FIG. 5

OLIGONUCLEOTIDES FOR DETECTING *STAPHYLOCOCCUS*

The present invention relates to the field of nucleic acid amplification. More particularly, the invention relates to oligonucleotide primers for amplifying the sequence or part of the sequence of a *Staphylococcus tuf* gene. In another aspect, the invention relates to a method for identifying one or more *Staphylococcus* species and/or strains which are present in a biological sample, such as a skin swab. In yet another aspect, the invention relates to the use of an oligonucleotide primer of the present invention for amplifying the sequence or part of the sequence of a *Staphylococcus tuf* gene. Kits which comprise an oligonucleotide primer of the present invention are also provided for carrying out the methods of the invention.

BACKGROUND OF THE INVENTION

Coagulase-negative staphylococcal species (CoNS) constitute an important part of the human skin microbiome. In particular, facultative anaerobic species such as *Staphylococcus epidermidis* and *Staphylococcus capitis* can be found on the skin of almost every human being. Studies have highlighted the prevalence of CoNS, which colonize mostly moist and sebaceous areas of the skin. In this regard, the CoNS species *S. epidermidis, S. capitis* and *S. hominis* occupy virtually every human skin site [1, 2]. Other CoNS species such as *S. haemolyticus, S. warneri, S. cohnii, S. simulans, S. auricularis, S. lugdunensis, S. massiliensis* and *S. pettenkoferi* can be found in lower amounts, varying from person to person and skin site to skin site [3-7]. Some other CoNS species such as *S. equorum* are primary found in food products [8], but are also transient colonizers of human skin.

Culture-dependent approaches to identify all microbial skin inhabitants are often biased, which means that the results obtained from such studies do often not reflect the true distribution of the individual members of the skin microbiota [9]. The bias is introduced due to the chosen growth media, as well as the conditions of growth, such as $O_2$ and $CO_2$ concentrations, growth temperature and cultivation time. Fast-growing organisms usually have a growth advantage and may directly or indirectly inhibit the growth of slow-growing organisms, in particular microaerophilic or anaerobic species [10].

Accordingly, culture-independent studies employing next-generation sequencing (NGS) have been used more frequently in recent years. Using 16S rRNA amplicon NGS, it was shown that the genus *Staphylococcus* is the third most abundant genus on the skin [11]. More recently, shotgun NGS unraveled the diversity of staphylococcal species on the skin, and also resolved the strain-level distribution of species such as *S. epidermidis* [1]. Culture-independent studies have not only revealed the diversity and individuality of the skin microbiota, but also have identified microbial "dark matter". For example, shotgun NGS resulted in many sequences that could not be assigned to any known microbial species. For instance, the study reported in reference [1] identified several uncharacterized genomes (assembled from shotgun NGS data) that belonged to unknown species, possibly species of the genera *Corynebacterium, Cutibacterium*, and *Staphylococcus*. Thus, it can be expected that several species exist on the skin that cannot be easily cultivated by standard conditions.

The detection and quantification of bacterial species, and in particular *Staphylococcus* species, in the skin microbiome of an individual is of utmost importance for understanding the mechanisms which contribute to the development of skin diseases or conditions like acne. It is assumed that in healthy skin, the different *Staphylococcus* species are well balanced with respect to each other and that disturbing this balance is causative for or at least contributes to the development of diseases. Accordingly, it is important to detect the different *Staphylococcus* species that occur on the skin of an individual and to determine their relative abundances to be able to provide methods for treating, ameliorating or preventing skin conditions which are tailored to the respective individual. Stated differently, the overall objective is a step towards personalized skin care.

Amplicon NGS approaches available to date for determining *Staphylococcus* species have made an essential contribution to reaching this objective. However, further improvements are required on the level of the means and methods that are used for detection. For example, it has been found that the primers used in commonly available amplicon NGS methods are able to detect only some species reliably while other species are not detected at all. Amplicon NGS techniques used for determining the *Staphylococcus* species in a given sample therefore provide an incomplete and hence incorrect picture of the microbiome that is analyzed. Therefore, methods are needed which allow for a more diverse detection of *Staphylococcus* species in a sample.

SUMMARY OF THE INVENTION

It has been found herein that by selecting appropriate primers, it is possible to obtain a more complete picture of the different *Staphylococcus* species and their relative abundances in a biological sample. These primers target the *tuf* gene, a gene that is present in all *Staphylococcus* species and encodes the elongation factor Tu. The primers described herein have been found to amplify part of the *tuf* gene sequence of essentially all *Staphylococcus* species that commonly occur on human skin. Consequently, it is possible to employ these primers in a universal approach that aims at the identification of all *Staphylococcus* species that are commonly present in a sample to be analyzed.

By using the primers of the invention, it was surprisingly found that numerous skin samples comprise the species *S. saccharolyticus* which appears to be a common member of the skin microbiome. This species has rarely been described to date; it was found on a few skin samples [13, 14], and like several other CoNS, the species has been described in case studies in association with a few infections in humans, such as bacteremia [15], soft tissue, bone and joint infections and implant-associated infections [12]. In the present studies using the novel primers, *S. saccharolyticus* was identified as the third most abundant species on the skin of the back. Although described as a slow-growing anaerobic species, a re-evaluation of its growth behaviour showed that this species can grow under toxic conditions in the presence of 5% $CO_2$. It can therefore be assumed that *S. saccharolyticus* was largely overlooked in previous studies due to the requirement for fastidious growth conditions.

This demonstrates that prior art methods have not been able so far to correctly reflect the level of diversity within the group of *Staphylococcus* bacteria that populate the human skin. As a result, these primers are disadvantageous when used for determining the composition of the skin microbiome. The primers of the present invention enable a more specific analysis in that they detect species that so far escaped analysis.

Thus, in a first aspect, the invention relates to an oligonucleotide primer comprising:

a) the nucleotide sequence of SEQ ID NO:1 or SEQ ID NO:2; or b) a sequence which is at least 85% identical to the nucleotide sequence of SEQ ID NO:1 or SEQ ID NO:2; or c) the complement of (a) or (b).

In one preferred embodiment of the invention, the primer comprises the nucleotide sequence of SEQ ID NO:1 or its complement. In another preferred embodiment, the primer comprises the nucleotide sequence of SEQ ID NO:2 or its complement. In addition, as will be understood by those skilled in the art, a limited degree of sequence variation relative to the nucleotide sequence of SEQ ID NO:1 or SEQ ID NO:2 or their complements may occur without affecting the functionality of the oligonucleotide primers. For example, sequence variants may be used having one or more (e.g. 1, 2, 3) substitutions, insertions or deletions of nucleotides relative to the sequence of SEQ ID NO:1 or SEQ ID NO:2 or their complements. The variant will have at least 85% sequence identity to the sequence of SEQ ID NO:1 or SEQ ID NO:2 or their complements, preferably at least 86%, 87%, 88%, 89%, 90%, 91%, 92%, 93%, 94%, 95%, 96%, 97%, 98%, or 99% sequence identity. In a particularly preferred aspect of the invention, the oligonucleotide probe consists of the sequence of SEQ ID NO:1 or SEQ ID NO:2.

In a particularly preferred embodiment, the invention relates to an oligonucleotide primer that comprises or consists of a) the nucleotide sequence of SEQ ID NO:1 or SEQ ID NO:2; or b) a sequence which differs from SEQ ID NO:1 or SEQ ID NO:2 by no more than 2 nucleotides, and more preferably no more than 1 nucleotide; or c) the complement of (a) or (b).

As used herein, the term oligonucleotide denotes a molecule consisting of at least 5 nucleotides, and preferably at least 10, 15, 20, 25, 30 or 35 nucleotides. The length of the molecule will be up to 35 nucleotides, preferably up to 40, 45, 50, 55, 60, 65, 70, 75 or 80 nucleotides. In other words, an oligonucleotide as defined herein will have a length of 10-70, more preferably 10-50, 15-50, 20-50 or 25-50 nucleotides.

The oligonucleotide primer of the present invention may include one or more sequences that are not complementary to the *Staphylococcus* target sequence, such as sequencing adaptors. In a preferred embodiment, the primer of the invention comprises adapter sequences for NGS. Suitable NGS adapter sequences are known in the art and comprise, e.g. the adapters used in the Illumina NGS sequencing kits.

Primer sequences with NGS adapter sequences are exemplary set forth in SEQ ID NO:3 and SEQ ID NO:4. Thus, the invention also relates to an oligonucleotide primer comprising:

a) the nucleotide sequence of SEQ ID NO:3 or SEQ ID NO:4; or b) a sequence which is at least 85% identical to the nucleotide sequence of SEQ ID NO:3 or SEQ ID NO:4; or c) the complement of (a) or (b).

In a preferred embodiment, the invention relates to an oligonucleotide primer comprising or consisting of:

a) the nucleotide sequence of SEQ ID NO:3 or SEQ ID NO:4; or b) a sequence which differs from SEQ ID NO:3 or SEQ ID NO:4 by no more than 2 nucleotides, and more preferably no more than 1 nucleotide; or c) the complement of (a) or (b).

In a particularly preferred embodiment of the invention, the primer of the invention consists of a sequence of any of SEQ ID NOs:1-4. The primers depicted in SEQ ID NOs:1 and 3 are forward primers which can be combined with corresponding reverse primers so as to form a primer pair that can be used for the amplification of the target sequence. The primers depicted in SEQ ID NOs:2 and 4 are reverse primers. Preferably, the primer of SEQ ID NO:1 is used in combination with the primer of SEQ ID NO:2, and the primer of SEQ ID NO:3 is used in combination with the primer of SEQ ID NO:4.

In a second aspect, the invention relates to a method for amplifying the sequence or part of the sequence of a *Staphylococcus tuf* gene, said method comprising:

a) obtaining nucleic acid from bacteria of the genus *Staphylococcus*, preferably genomic DNA;

b) amplifying the nucleic acid with at least one oligonucleotide primer as defined hereinabove; and c) optionally, sequencing the amplified nucleic acid.

In a first step of the above method, nucleic acid is obtained from bacteria of the genus *Staphylococcus*. The nucleic acid can be DNA, RNA or a mixture of DNA and RNA. Preferably, the nucleic acid which is subjected to the method of the invention will comprise DNA derived from bacteria of the genus *Staphylococcus*, more preferably genomic DNA. The nucleic acid used for amplification preferably contains nucleic acids, preferably genomic DNA molecules, from more than one *Staphylococcus* species or strain, i.e. from two, three, four, five or more *Staphylococcus* species or strains. This means that the nucleic acid used in step (a) of the method of the second aspect of the invention can be a mixture of nucleic acids derived from different *Staphylococcus* species or strains.

For example, the nucleic acid may be genomic DNA isolated from a group of bacteria that are present colonizes a tissue, a tissue surface, e.g. the skin surface, or a body fluid of a subject, preferably a human subject. This means that the nucleic acid can be a mixture of nucleic acids of the bacteria that form the microbiome of a specific tissue, tissue surface, or body fluid. As used herein, the term microbiome refers to the entirety of bacterial species that colonize a particular area of the skin, e.g. the facial skin. In a particular preferred embodiment, the nucleic acid used in step (a) of the method of the second aspect of the invention is genomic DNA of the microbiome of the human skin, more preferably the human facial skin or the skin of the back or armpit. In other embodiments, the nucleic acid is genomic DNA of the microbiome of a body fluid. Such body fluid may include whole blood, blood serum, blood plasma, urine, sputum, bronchial lavage, liquor, and the like.

Samples of the microbiome of a tissue or body fluid can be obtained by commonly known methods, e.g. biopsy, venipuncture and nasal or skin swabs. In a particularly preferred embodiment, the nucleic acid sample is genomic DNA isolated from the microbiome of the human skin, such as the facial skin or the skin of the back or armpit. The microbiome sample preferably is a nasal or skin swab.

After the microbiome sample has been obtained from the individual, e.g. a skin swab, the nucleic acid of the bacteria that are present in the sample can be obtained by using commonly available kits, e.g. kits for the purification of DNA or RNA (available e.g. from Qiagen, Hilden, Germany). These kits normally provide for the lysis of the bacterial cells in the sample, selective binding of the genomic DNA to a matrix, purification of the bound DNA by removal of proteins and other cell components, and elution of the purified genomic DNA. Methods of isolating and purifying genomic DNA from bacteria are well known to a person of skill.

In a subsequent step of the method of the second aspect of the invention, the nucleic acid obtained in step (a) is amplified by use of at least one oligonucleotide primer as defined hereinabove, i.e. an oligonucleotide primer comprising:

a) the nucleotide sequence of any of SEQ ID NOs:1-4;
b) a sequence which is at least 85% identical to the nucleotide sequence of any of SEQ ID NOs:1-4 or a sequence which differs from of any of SEQ ID NOs:1-4 by no more than 2 nucleotides, and more preferably no more than 1 nucleotide; or
c) the complement of (a) or (b).

In a preferred embodiment, the nucleic acid is amplified in step (b) by using both (i) a primer comprising the nucleotide sequence of SEQ ID NO:1 (or the complement thereof) or a sequence which is at least 85% or at least 90% identical to any of those, and (ii) a primer comprising the nucleotide sequence of SEQ ID NO:2 (or the complement thereof) or a sequence which is at least 85% or at least 90% identical to any of those. Accordingly, it is preferred that the nucleic acid is amplified in step (b) with (i) a first primer comprising:
  a) the nucleotide sequence of SEQ ID NO:1; or
  b) a sequence which is at least 85%, more preferably at least 90%, identical to the nucleotide sequence of SEQ ID NO:1 or which differs from SEQ ID NO:1 by no more than 1 or 2 nucleotides; or
  c) the complement of (a) or (b); and
(ii) a second primer comprising:
  a) the nucleotide sequence of SEQ ID NO:2; or
  b) a sequence which is at least 85%, more preferably at least 90%, identical to the nucleotide sequence of SEQ ID NO:2 or which differs from SEQ ID NO:2 by no more than 1 or 2 nucleotides; or
  c) the complement of (a) or (b).

Where the nucleic acid in the nucleic acid sample is DNA, the amplification can be achieved by a polymerase chain reaction (PCR). A PCR is an enzymatic reaction for increasing the amount or concentration of a DNA sequence which is catalyzed by a thermostable DNA-dependent DNA polymerase. The primers are complementary to one strand of the double-stranded target sequence. For amplification, the double-stranded target sequence is denatured so as to allow annealing of the primers. Following annealing, the primers are extended by means of the DNA polymerase to form a new pair of complementary strands. The steps of denaturation, primer annealing, and polymerase extension are repeated several times, e.g. 15-35 times, to obtain a high amount or concentration of the target DNA sequence. PCR amplification methods are well-known to the skilled person, and PCR kits are purchasable from many different manufacturers. The oligonucleotide primers defined above can be used for amplification of a part of the *Staphylococcus tuf* gene.

Alternatively, the oligonucleotide primers of the present invention may also be used in an RT-PCR reaction. Where the nucleic acid extracted from the biological sample is RNA (e.g. total RNA or mRNA), the first step of the amplification is a reverse transcription reaction (RT). In this reaction, the RNA is transcribed into cDNA by means of a reverse transcriptase enzyme. Reverse transcription can be achieved by use of a sequence specific primer or an oligo-d(T) primer which is complementary to the poly (A) tail of the RNA. The cDNA generated by the reverse transcriptase is then used as a template in a subsequent PCR reaction. An amplification reaction comprising a reverse transcription reaction and a subsequent PCR amplification reaction is referred to as "RT-PCR" herein. According to the present invention, the RT-PCR can be performed as a one-step or two-step RT-PCR. The primers defined above can be used for specifically amplifying the *Staphylococcus tuf* gene when starting from a RNA preparation that was derived from a microbiome that is colonized by *Staphylococcus* species and/or strains.

In an optional step of the method of the second aspect of the invention, the amplified nucleic acid obtained from step (b) is subjected to sequencing which means that the nucleotide sequence of the amplicons derived from step (b) is determined. In principle, any method known in the art for sequencing nucleic acids, in particular DNA, can be used including Maxam-Gilbert sequencing, Sanger sequencing, Shotgun sequencing, and next-generation sequencing (NGS), pyrosequencing, nanopore sequencing and the like. In a preferred embodiment, the sequencing step is performed by NGS, for example, by the sequencing-by-synthesis (SBS) technology of Illumina. Sequencing kits for NGS are available from many different manufacturers.

In a third aspect of the invention, the invention further relates to a method for identifying one or more *Staphylococcus* species and/or strains which are present in a biological sample, comprising a) obtaining a nucleic acid from bacteria of the genus *Staphylococcus*, preferably genomic DNA;
b) amplifying the nucleic acid with at least one oligonucleotide primer as described hereinabove;
c) sequencing the amplified nucleic acid;
d) comparing the sequences obtained in step (c) with reference sequences from different *Staphylococcus* species and/or strains; and
e) assigning the sequences obtained in step (c) to a *Staphylococcus* reference sequence, thereby identifying the species and/or strains.

Accordingly, the method of the third aspect of the invention comprises all steps of the method of the second aspect of the invention (with the sequencing step being mandatory) and, in addition, steps in which the sequences are compared to reference sequences, i.e. known sequences of the *tuf* gene of a defined *Staphylococcus* species and/or strain.

Steps (a)-(c) of the method of the third aspect of the invention are carried out as described in relation to steps (a)-(c) of the method of the second aspect of the invention.

In the subsequent step (d) of the above method of the third aspect of the invention, the nucleic acid sequences determined in step (c) are compared to reference sequences from a plurality of different *Staphylococcus* species and/or strains. Preferably, the sequences determined in step (c) can be compared to a database that harbours the nucleotide sequences of a plurality of *tuf* genes derived from different *Staphylococcus* species and/or strains. Preferably, the database will contain at least 10, least 20, least 30, least 40, least 50, least 60, least 70, least 80 or more different complete or partial *tuf* gene sequences derived from different *Staphylococcus* species and/or strains. A suitable database is provided in the attached sequence listing that comprises the nucleotide sequences of 96 *tuf* genes. Accordingly, in a preferred embodiment, the sequences determined in step (c) of the above method are compared with two or more of the reference sequences set forth in SEQ ID NOs:5-100, more preferably with at least 5, at least 10, at least 15, at least 20, at least 25, at least 30, at least 35, at least 40, at least 45, at least 50, least 55, at least 60, at least 65, at least 70, at least 75, least 80, at least 85, at least 90, at least 95 or more of these sequences. It is particularly preferred that the sequences determined in step (c) of the method of the third aspect of the invention are compared with a database which harbours all of the nucleotide sequences set forth in SEQ ID NOs:5-100.

Of course, the sequences determined in step (c) can also be compared to a freely accessible database that comprises all different types of genomic DNA sequences from different bacterial organisms, such as the GenBank database.

The comparison will allow assigning a sequence determined in step (c) of the method to a specific *Staphylococcus* reference sequence derived from a defined *Staphylococcus* species or strain, thereby identifying the species and/or strains. For example, a nucleotide sequence determined in step (c) of the claimed method can be assigned to a specific *Staphylococcus* reference sequence if the sequence identity on the nucleotide level is at least 98%, preferably at least 99%. In a particularly preferred embodiment, the nucleotide sequence determined in step (c) of the above method can be assigned to a specific *Staphylococcus* reference sequence if the sequence identity on the nucleotide level is 100%.

Preferably, the sequence identity is determined over a length of at least 50 nucleotides, more preferably at least 100 nucleotides, at least 150 nucleotides, at least 200 nucleotides, at least 250 nucleotides, at least 300 nucleotides, at least 350 nucleotides, at least 400 nucleotides, or at least 450 nucleotides of the *tuf* gene.

In one preferred embodiment, the nucleotide sequence determined in step (c) of the claimed method can be assigned to a specific *Staphylococcus* reference sequence if the sequence identity on the nucleotide level is at least 98% over a length of at least 200 nucleotides, more preferably at least 300 nucleotides, and even more preferably at least 400 nucleotides. For example, the sequence identity of at least 98% is measured over a length of between 200-400 nucleotides, preferably between 200-300 nucleotides.

In another preferred embodiment, the nucleotide sequence determined in step (c) of the claimed method can be assigned to a specific *Staphylococcus* reference sequence if the sequence identity on the nucleotide level is at least 99% over a length of at least 200 nucleotides, more preferably at least 300 nucleotides, and even more preferably at least 400 nucleotides. For example, the sequence identity of at least 99% is measured over a length of between 200-400 nucleotides, preferably between 200-300 nucleotides.

In yet another preferred embodiment, the nucleotide sequence determined in step (c) of the claimed method can be assigned to a specific *Staphylococcus* reference sequence if the sequence identity on the nucleotide level is at least 100% over a length of at least 200 nucleotides, more preferably at least 300 nucleotides, and even more preferably at least 400 nucleotides. For example, the sequence identity of at least 100% is measured over a length of between 200-400 nucleotides, preferably between 200-300 nucleotides.

Sequence identity between two or more nucleotide sequences can be determined by using mathematical algorithms. Algorithm used sequences comparison are well know in the art and include the algorithm of Karlin and Altschul, 1990, Proc. Natl. Acad. Sci. USA 87:2264-2268, and the modified algorithm of Karlin and Altschul, 1993, Proc. Natl. Acad. Sci. USA 90:5873-5877. These algorithms are incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid of interest. Another example of a mathematical algorithm that can be used for the comparison of nucleotide sequences is the algorithm of Myers and Miller, CABIOS (1989). This algorithm is used in the ALIGN program (version 2.0) which is part of the GCG sequence alignment software package. Additional algorithms for sequence analysis include FASTA (Pearson and Lipman, 1988, Proc. Natl. Acad. Sci. USA 85:2444-8).

In order to determine the sequence identity between two nucleotide sequences, these sequences are usually aligned for optimal comparison. For example, gaps can be introduced in the sequence of a first nucleotide sequence for optimal alignment with a second nucleotide sequence. The nucleotides at corresponding nucleotide positions are then compared. If identical nucleotides occur in corresponding positions in the first and second nucleotide sequence, the sequences are identical at that position.

By assigning all of the sequences identified in step (c) of the above method of the third aspect of the invention to a single *Staphylococcus* reference sequence of a defined species or strain, it is possible to determine all the different *Staphylococcus* species and/or strains that occur within the microbiome from which the ample was derived. In this way, it is possible to identify essentially all of the distinct *Staphylococcus* species and/or strains that occur, e.g. on a defined skin area of an individual, such as the facial skin.

Apart from a merely qualitative identification in step (e), the method can also b adapted to provide a quantitative identification. As used herein, a "qualitative" identification means that the different nucleotide sequences determined in step (c) of the method are assigned to a defined *Staphylococcus* species and/or strain such that all species and/or strains present in the original sample are determined. In contrast, a "quantitative" identification means that not only the occurrence of a species and/or strain I determined, but also the relative or absolute abundance of the respective species and/or strain.

For example, it will be advantageous under certain conditions to determine the relative abundance of a *Staphylococcus* species on the skin. For example, it is known that a high concentration of the species *S. hominis* on the skin of the armpit is regularly associated with an unpleasant sweat odour, whereas *S. epidermidis* produces significantly less odour. Accordingly, knowledge of the relative abundances of *S. hominis* and *S. epidermidis* on this particular skin area of an individual can assist in the selection of a deodorant that is most suitable for the individual. For example, if the above method of the third aspect of the invention reveals that the concentration of *S. hominis* is high, a stronger deodorant can be selected for this individual. In this way, the method can contribute to a personalized skin care.

In a fourth aspect, the invention also relates to the use of an oligonucleotide primer as defined above for amplifying the sequence or part of the sequence of a *Staphylococcus tuf* gene. Such use may include, as indicated elsewhere herein, the amplification of nucleic acid obtained from a mixture of *Staphylococcus* species and/or strains in order to identify and distinguish those species and/or strains from each other. More particularly, the invention also relates to the use of an oligonucleotide primer as defined above for determining the composition of the *Staphylococcus* population that occurs within a given microbiome of an individual, i.e. the microbiome of the facial skin. In this way, it is possible to tailor skin care compositions in accordance with the presence and abundances of different *Staphylococcus* species and/or strains in a defined skin area of the individual. As explained elsewhere herein, the determination can be a qualitative and/or quantitative determination.

In a fifth aspect, the invention relates to a method for identifying the presence of *Staphylococcus saccharolyticus* in a biological sample, said method comprising a) obtaining a nucleic acid from a biological sample that is supposed to comprise bacteria of the genus *Staphylococcus*, preferably genomic DNA;
b) amplifying the nucleic acid with at least one oligonucleotide primer as described hereinabove;
c) sequencing the amplified nucleic acid;
d) comparing the sequences obtained in step (c) with reference sequences from different *Staphylococcus* species and/or strains; and
e) assigning the sequences obtained in step (c) to a *Staphylococcus saccharolyticus* reference sequence, thereby identifying the presence of *Staphylococcus saccharolyticus* in the biological sample.

As explained elsewhere herein, the biological sample can be a tissue sample, such as a tissue biopsy or swab, or a body fluid sample, such as whole blood, blood serum, blood plasma, urine, sputum, bronchial lavage, liquor, and the like. Preferably, the biological sample is a tissue swab, such as a swab of the facial skin or the skin of the back or armpit.

In a sixth aspect, the invention relates to a kit for amplifying the sequence or part of the sequence of a *Staphylococcus tuf* gene, said kit comprising a) at least one oligonucleotide primer as described hereinabove; and
b) means for performing a nucleic acid amplification and/or sequencing reaction.

The invention also pertains to a kit for carrying out any of the methods referred to hereinabove. The kit comprises at least one of the oligonucleotide primers of the invention, e.g. an oligonucleotide primer comprising or consisting of the nucleotide sequence of SEQ ID NO:1 or an oligonucleotide primer comprising or consisting of the nucleotide sequence of SEQ ID NO:2. Preferably, the kit includes a first oligonucleotide primer comprising: a) the nucleotide sequence of SEQ ID NO:1; or b) a sequence which is at least 85%, preferably at least 85%, preferably at least 90%, identical to the nucleotide sequence of SEQ ID NO:1; or c) the complement of (a) or (b); and a second primer comprising a) the nucleotide sequence of SEQ ID NO:2; or b) a sequence which is at least 85%, preferably at least 90%, identical to the nucleotide sequence of SEQ ID NO:2; or c) the complement of (a) or (b).

In a most preferred embodiment, the kit includes a first oligonucleotide primer comprising the nucleotide sequence of SEQ ID NO:1 or a complement thereof and a second oligonucleotide primer comprising the nucleotide sequence of SEQ ID NO:2 or a complement thereof. The kit also includes means for performing a nucleic acid amplification and/or a sequencing reaction. Preferably, the kit will comprise buffers and reagents that are suitable for amplifying a bacterial nucleic acid, such as DNA. The kit may include, for example, suitable buffers or enzymes like one or more polymerases. The kit may also include suitable sequencing adapters for NGS sequencing.

BRIEF DESCRIPTION OF THE DRAWINGS

FIG. 2 shows the results of the diversity analysis of staphylococcal species in back skin samples based on amplicon NGS data. FIG. 2B shows the average of relative abundancies of 12 staphylococcal species. FIG. 2C shows the relative abundancies of the four most prominent species.

FIG. 5 shows the sequence of the PCR primer used for comparison. The sequence of these primers is depicted in SEQ ID NO:101-104.

DETAILED DESCRIPTION OF EXEMPLARY EMBODIMENTS OF THE INVENTION

EXAMPLES

Figures 1, 2A:
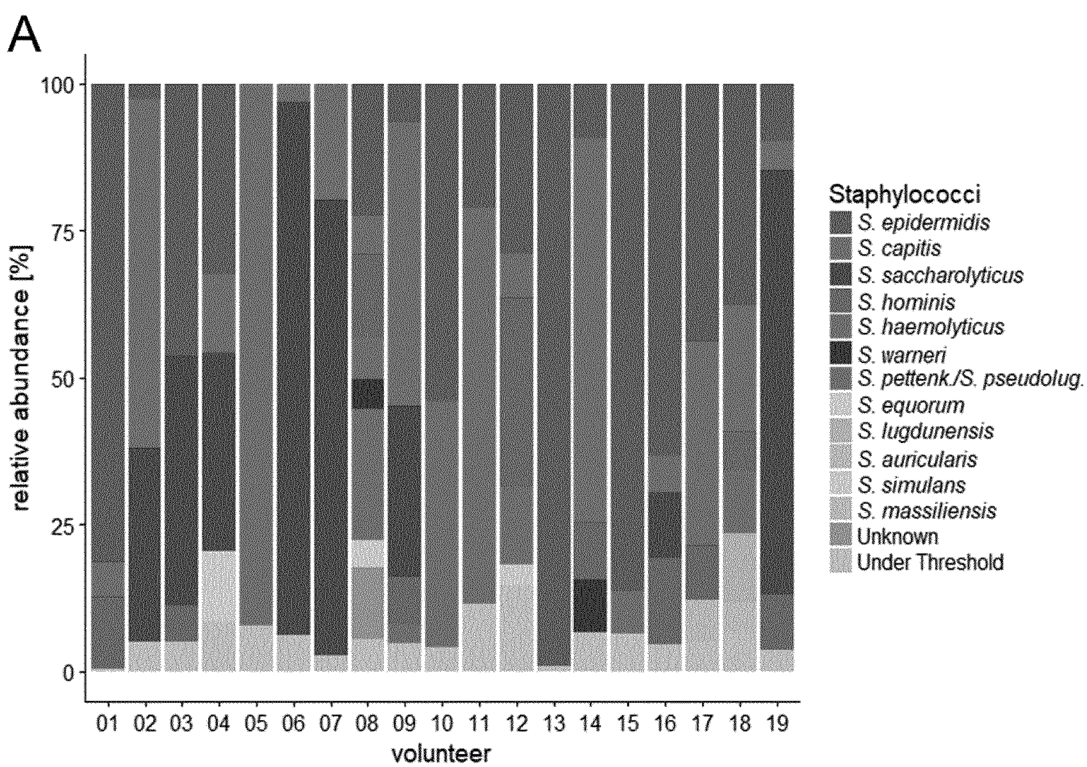
FIG. 1 shows the sequence of the PCR primer used for amplifying the *tuf* gene. The *tuf*-specific sequence parts of these primers are depicted in SEQ ID NO:1 and SEQ ID NO:2. The primers that include the MiSeq adapter sequences are depicted in SEQ ID NO:3 and SEQ ID NO:4.
FIG. 2A shows the relative abundancies of species for each volunteer.

The present invention is further illustrated by the following examples, which in no way should be construed as limiting. The entire contents of all of the references (including literature references, issued patents, published patent applications, and co pending patent applications) cited throughout this application are hereby expressly incorporated by reference.

Example 1: Skin Sample Preparation and Processing

Skin swab samples from 19 volunteers (female, n=11; male, n=8) with an age range of 22-43 years were taken from the upper back. None of the volunteers had a history of skin disease; none had undergone treatment with topical medicine or antibiotics during the last six months. Written informed consent was obtained from all volunteers and the study was approved by International Medical & Dental Ethics Commission GmbH (IMDEC).

An area of 25 $cm^2$ on the upper back was sampled with a cotton swab pre-moistened in aqueous sampling buffer containing disodium phosphate (12.49 g/L, Merck), potassium dihydrogen phosphate (0.63 g/L, Merck) and Triton X-100 (1 g/L, Sigma). After sampling, the swab was transferred into a sterile tube containing 2 mL of sampling buffer; the swap was viscously shacked in the sampling buffer and then removed. Skin swab material was stored at −20° C. until further processing.

DNA was extracted from the 2 mL sample by use of the DNeasy PowerSoil Kit (QIAGEN) following the manufacturer's protocol, with an additional cell lysis step with lysostaphin (0.05 mg/mL, Sigma) and lysozyme (9.5 mg/mL, Sigma) prior to extraction. DNA concentrations were measured by using Qubit with the Qubit dsDNA HS Assay (ThermoFisher Scientific). The DNA obtained from the extraction process was amplified using *tuf*-specific primers that contained MiSeq adapter sequences:

```
tuf2_miseq_F red
                                        (SEQ ID NO: 1)
5'-ACAGGCCGTGTTGAACGTG-3'

tuf2_miseq_R red
                                        (SEQ ID NO: 2)
5'-ACAGTACGTCCACCTTCACG-3'

tuf2_miseq_F
                                        (SEQ ID NO: 3)
5'-TCGTCGGCAGCGTCAGATGTGTATAAGAGACAGACAGGCCGTGTTG
AACGTG-3'

tuf2_miseq_R
                                        (SEQ ID NO: 4)
5'-GTCTCGTGGGCTCGGAGATGTGTATAAGAGACAGACAGTACGTCCA
CCTTCACG-3'
```

The primers used for the PCR reaction are shown in SEQ ID NO:3 and SEQ ID NO:4. The *tuf*-specific sequence parts of these primers are depicted in SEQ ID NO:1 and SEQ ID NO:2. The primers are also shown in FIG. 1. PCR reaction mixtures were made in a total volume of 25 μl and comprised 5 μl of DNA sample, 2.5 μl AccuPrime PCR Buffer II (Invitrogen), 1.5 μl of each primer (10 μM) (DNA Technology), 0.15 μl AccuPrime Taq DNA Polymerase High Fidelity (Invitrogen), and 14.35 μl of PCR grade water. PCR was performed using the following cycle conditions: an initial denaturation at 94° C. for 2 min, followed by 35 cycles of denaturation at 94° C. for 20 sec, annealing at 55° C. for 30 sec, elongation at 68° C. for 1 min, and a final elongation step at 72° C. for 5 min. The PCR products were verified on an agarose gel and purified using the Qiagen Generead™ Size Selection kit. The concentration of the purified PCR product was measured with a NanoDrop 2000 spectrophotometer (Thermo Scientific).

Example 2: Next Generation Sequencing

The PCR products obtained in Example 1 were used to attach indices and Illumina sequencing adapters using the Nextera XT Index kit (Illumina, San Diego). Index PCR was performed using 5 μl of template PCR product, 2.5 μl of each index primer, 12.5 μl of 2× KAPA HiFi HotStart ReadyMix and 2.5 μl PCR grade water. Thermal cycling scheme was as follows: 95° C. for 3 min, 8 cycles of 30 s at 95° C., 30 s at 55° C. and 30 s at 72° C. and a final extension at 72° C. for 5 min. Quantification of the products was performed using the Quant-iT dsDNA HS assay kit and a Qubit fluorometer following the manufacturer's instructions. MagSi-NGS$^{PREP}$ Plus Magnetic beads (Steinbrenner Laborsysteme GmbH, Wiesenbach, Germany) were used for purification of the indexed products as recommended by the manufacturer and normalization was performed using the Janus Automated Workstation from Perkin Elmer (Perkin Elmer, Waltham Massachusetts, USA). Sequencing was conducted using Illumina MiSeq platform using dual indexing and MiSeq reagent kit v3 (600 cycles) as recommended by the manufacturer.

FASTQ sequences obtained after demultiplexing the reads and trimming the primers were imported into QIIME2 (v. 2019.7) [16]. Sequences with average quality score lower than 20 or containing unresolved nucleotides were removed from the dataset with the split_libraries_fastq.py script from QIIME. The paired-end reads were denoised and chimeras removed with DADA2 via QIIME2 and a feature table was generated [17]. These features were then clustered with VSEARCH at a threshold of 99% identity against an in-house generated *tuf* allele database that covered all *tuf* alleles from all staphylococcal genomes available in GenBank (as of December 2019). Data were normalized and figures were prepared in R with the packages ggplot2 [18] and gplots [19].

By the above approach, a total of twelve different staphylococcal species were identified on the back skin of the test persons (FIG. 2A). Most samples contained two or more staphylococcal species. The back skin of only two volunteers harboured a single species only, *S. capitis* and *S. epidermidis*, respectively. The four most abundant staphylococcal species identified were *S. epidermidis* (average abundancy 34.0%) and *S. capitis* (26.6%), followed by *S. saccharolyticus* (20.5%) and *S. hominis* (6.5%). This is shown in FIG. 2B. In eight out of 19 samples (42%) *S. saccharolyticus* could be identified. If present in the back skin sample, *S. saccharolyticus* was a dominant species; from 10.9% up to 90.4% of the total reads were originating from *S. saccharolyticus* in such samples (FIG. 2C).

Example 3: Primer Comparison

To compare the efficiency and the resolution capacity of the primers of SEQ ID NO:1 and SEQ ID NO:2, the primers were tested in parallel along with two alternative primer sets to detect different staphylococcal species in bacterial mock communities. Specifically, genomic DNA of 18 strains was used to create two mock communities (M1 and M2). All strains belonged to staphylococcal species commonly found on human skin. The DNA was combined in equimolar ratios, with 0.05 ng or 50 ng DNA of each strain.

Mock community M1 contained the following nine strains: *S. epidermidis* ATCC 12228, *S. hominis* HAA31, *S. capitis* HAF22, *S. aureus* DSM 20231, *S. warneri* HAA271, *S. haemolyticus* HAA11, *S. saprophyticus* HAF121, *S. simulans* HAA294 and *S. saccharolyticus* 13T0028. Mock community M2 contained a total of 18 strains, namely the nine strains M1 plus one additional strain for each species, i.e. *S. hominis* DSM 20328, *S. capitis* DSM 20325, *S. warneri* DSM 20316, *S. epidermidis* NCIB 11536, *S. haemolyticus* DSM 20263, *S. hominis* HAB38, *S. epidermidis* HAF81, *S. epidermidis* HAB176 and *S. saccharolyticus* DVP4 17 2404.

The primers set out in Example 1 above was compared to two comparative primer sets. The first comparative primer set was directed to the staphylococcal rpsK gene that encodes the 30S ribosomal protein S11 [27]. These primers had the following sequences:

```
rpsk forw
                                      (SEQ ID NO: 101)
5'-TGGCACGTAAACAAGTATC-3'

rpsk rev
                                      (SEQ ID NO: 102)
5'-GACGACGTTTTGGTGGAC-3'
```

The second comparative primer set ("*tuf*-alt") was directed to the staphylococcal *tuf* gene like the primers of the present invention. The amplicon targets of the *tuf*-alt primers overlap with the target of the primers of the invention. The *tuf*-alt primers had the following sequences (note that the nucleotide in position 2 of the *tuf*-alt reverse primer is inosine which is a universal base that is able to bind any other base):

```
tuf-alt forw
                                    (SEQ ID NO: 103)
5'-GGCCGTGTTGAACGTGGTCAAATC-3'

tuf-alt rev
                                    (SEQ ID NO: 104)
5'-TIACCATTTCAGTACCTTCTGGTAA-3'
```

The primer pairs SEQ ID NO:1 and 2, SEQ ID NO:101 and 102, and SEQ ID NO:103 and 104 were used to amplify the above DNA mixtures of the two mock communities M1 and M2. Briefly, PCR reaction mixtures were made in a total volume of 25 μl and comprised 5 μl of DNA sample, 2.5 μl AccuPrime PCR Buffer II (Invitrogen, Waltham, MA, USA), 1.5 μl of each primer (10 μM) (DNA Technology, Risskov, Denmark), 0.15 μl AccuPrime Taq DNA Polymerase High Fidelity (Invitrogen, Waltham, MA, USA), and 14.35 μl of PCR grade water. The PCR reaction was performed using the following cycle conditions: an initial denaturation at 94° C. for 2 min, followed by 35 cycles of denaturation at 94° C. for 20 sec, annealing at 55° C. for 30 sec, elongation at 68° C. for 1 min, and a final elongation step at 72° C. for 5 min. PCR products were verified on an agarose gel and purified using the Qiagen Generead Size Selection kit (Qiagen, Hilden, Germany). The concentration of the purified PCR products was measured with a NanoDrop 2000 spectrophotometer (ThermoFisher Scientific, Waltham, MA, USA). PCR products were subjected to next generation sequencing as described above.

Figure 3:
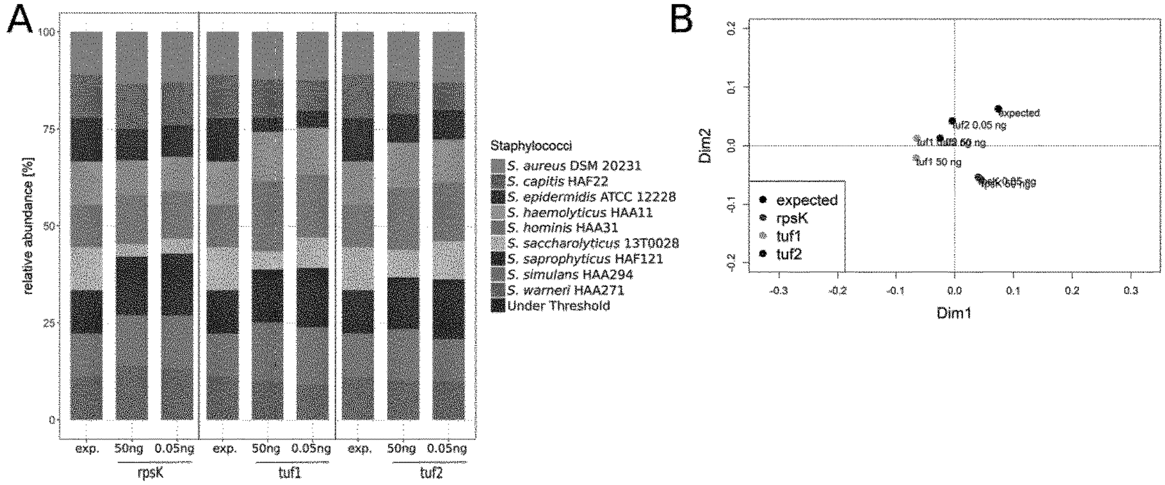
FIG. 3 shows the relative abundancies of staphylococcal species within the mock community M1, determined by three different NGS primer pairs. Relative abundancies of staphylococcal species in the mock community M1 were determined with the rpsK, tuf1, and tuf2 schemes. (A) Stacked bar plots of relative abundances of mock community M1 samples. (B) PCoA of Bray Curtis dissimilarity of the expected sample composition and mock community M1 analysed with the rpsK, tuf1 and tuf2 primer pairs.

For mock community M1, the comparison revealed that all three primer pairs were able to identify and distinguish each of the nine species. The rpsK (primers SEQ ID NO:101 and 102) and *tuf*-alt (primers SEQ ID NO:103 and 104) primer pairs slightly underrepresented *S. saccharolyticus* and *S. epidermidis*, respectively (see FIG. 3A). A principal coordinate analysis (PCoA) plot of Bray Curtis dissimilarity was constructed to examine how accurate each primer pair can represent the expected staphylococcal composition of community M1. The *tuf* primer pair (primers SEQ ID NO:1 and 2) represented the expected sample composition more accurately than the other two primer pairs. The experiment was repeated with different DNA input amounts, varying from 0.05 ng to 50 ng DNA per strain. The DNA input amount did only mildly influence the detected relative abundancies by the three primer pairs (FIGS. 3A and B).

Figure 4:
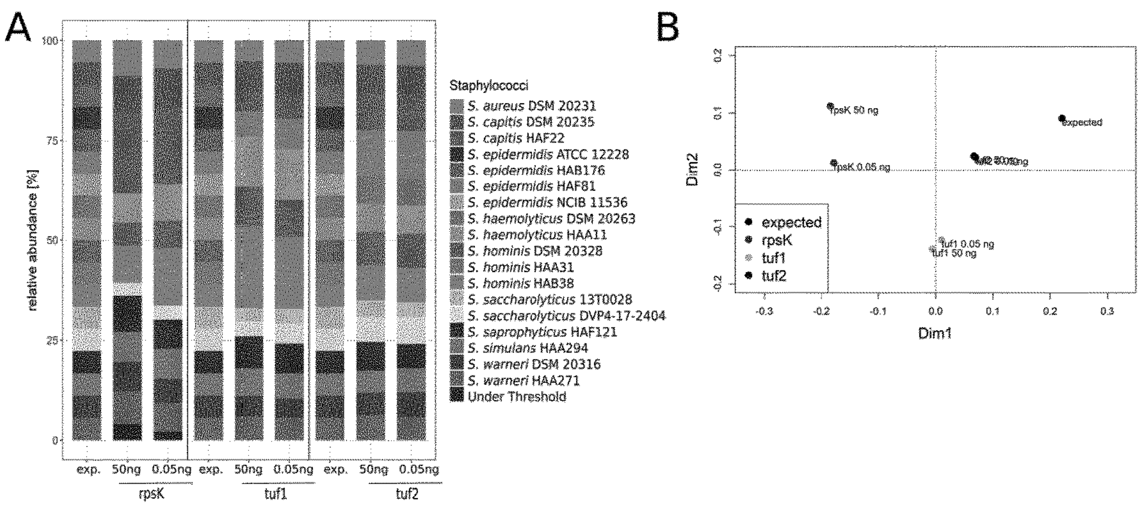
FIG. 4 shows the relative abundancies of staphylococcal species within the mock community M2, determined by three different NGS primer pairs. (A) Stacked bar plots of relative abundances of mock community M2 samples. (B) PCoA of Bray Curtis dissimilarity of the expected sample composition and mock community M2 analysed with the rpsK, tuf1 and tuf2 primer pairs.

For mock community M2, the theoretical resolution power of each primer pair regarding the M2 community was first calculated. The three target alleles of each of the 18 genomes present in M2 mixture were extracted and built into phylogenetic trees. The trees showed that the rpsK primer pair (primers SEQ ID NO:101 and 102), the *tuf*-alt (primers SEQ ID NO:103 and 104) primer pair, and the *tuf* primer pair (primers SEQ ID NO:1 and 2) should distinguish 12, 14 and 16 strains, respectively. Thus, in silico, the *tuf* primer pair is therefore superior in resolution power. Next, the three primer pairs were applied to analyse the mock community M2. The rpsK primer pair detected eleven strains, while the *tuf*-alt and *tuf* primer pairs detected 13 strains and 14 strains, respectively (see FIG. 4A). The PCoA plot from Bray Curtis dissimilarity showed that the expected sample composition was best reflected by the *tuf* primer pair (see FIGS. 4A and 4B).

In summary, all three primer pairs identified the staphylococcal populations of the mock communities accurately, regardless of the respective DNA input amounts. On the species level, the rpsK and *tuf*-alt primer pairs had problems to detected *S. saccharolyticus* accurately in all samples, while the *tuf* primer pairs was able to detect this species. In addition, the *tuf*-alt primers underrepresented *S. epidermidis* in both mock communities. In contrast, the data produced by the *tuf* primer pairs showed the highest sub-species diversity and could distinguish best between *S. epidermidis* alleles. Furthermore, the alpha diversity of mock community samples analysed with the *tuf* primer pairs matched best with the actual sample composition.

LITERATURE

1. Oh, J., et al., *Biogeography and individuality shape function in the human skin metagenome*. Nature, 2014. 514(7520): p. 59-64.
2. Kloos, W. E. and M. S. Musselwhite, *Distribution and persistence of Staphylococcus and Micrococcus species and other aerobic bacteria on human skin*. Appl Microbiol, 1975. 30(3): p. 381-5.
3. Schleiferi, K. H. K., W. E., *Isolation and Characterization of Staphylococci from Human Skin I. Amended Descriptions of Staphylococcus epidermidis and Staphylococcus saprophyticus and Descriptions of Three New Species: Staphylococcus cohnii, Staphylococcus haemolyticus, and Staphylococcus xylosus*. INT J SYST EVOL MICR, 1975. 25(1): p. 50-61.
4. Kloos, W. E. S., K. H., *Staphylococcus auricularis* sp. *nov.: an Inhabitant of the Human External Ear*. Int J Syst Bacteriol, 1983. 33(1): p. 9-14.
5. Bieber, L. and G. Kahlmeter, *Staphylococcus lugdunensis in several niches of the normal skin flora*. Clin Microbiol Infect, 2010. 16(4): p. 385-8.
6. Zong, Z., *The newly-recognized species Staphylococcus massiliensis is likely to be part of the human skin microflora*. Antonie Van Leeuwenhoek, 2012. 101(2): p. 449-51.
7. Mansson, E., et al., *Genomic relatedness of Staphylococcus pettenkoferi isolates of different origins*. J Med Microbiol, 2017. 66(5): p. 601-608.
8. Meugnier, H., et al., *Identification and ribotyping of Staphylococcus xylosus and Staphylococcus equorum strains isolated from goat milk and cheese*. Int J Food Microbiol, 1996. 31(1-3): p. 325-31.
9. Dickson, R. P., et al., *Analysis of culture-dependent versus culture-independent techniques for identification of bacteria in clinically obtained bronchoalveolar lavage fluid*. J Clin Microbiol, 2014. 52(10): p. 3605-13.
10. Kong, H. H. and J. A. Segre, *Skin microbiome: looking back to move forward*. J Invest Dermatol, 2012. 132(3 Pt 2): p. 933-9.
11. Grice, E. A., et al., *Topographical and temporal diversity of the human skin microbiome*. Science, 2009. 324(5931): p. 1190-2.
12. Bruggemann, H., et al., *Staphylococcus saccharolyticus Isolated From Blood Cultures and Prosthetic Joint Infections Exhibits Excessive Genome Decay*. Front Microbiol, 2019. 10: p. 478.
13. Evans, C. A., K. L. Mattern, and S. L. Hallam, *Isolation and identification of Peptococcus saccharolyticus from human skin*. J Clin Microbiol, 1978. 7(3): p. 261-4.
14. Evans, C. A. and K. L. Mattern, *Individual differences in the bacterial flora of the skin of the forehead: Peptococcus saccharolyticus*. J Invest Dermatol, 1978. 71(2): p. 152-3.
15. Steinbrueckner, B., et al., *Facing a mysterious hospital outbreak of bacteraemia due to Staphylococcus saccharolyticus*. J Hosp Infect, 2001. 49(4): p. 305-7.

16. Bolyen, E., et al., *Reproducible, interactive, scalable and extensible microbiome data science using QIIME* 2. Nat Biotechnol, 2019. 37(8): p. 852-857.
17. Callahan, B. J., et al., *DADA2: High-resolution sample inference from Illumina amplicon data*. Nat Methods, 2016. 13(7): p. 581-3.
18. Wickham, H., *ggplot2: Elegant Graphics for Data Analysis*. Springer-Verlag New York, 2009.
19. Warnes, G. R. B., B.; Bonebakker, L.; Gentleman, R.; Huber, W.; Liaw, A.; Lumley, T.; Maechler, M.; Magnusson, A.; Moeller, S.; Schwartz, M.; Venables, B., *gplots: Various R Programming Tools for Plotting Data*. 2020.
20. Oh, J., et al., *Temporal Stability of the Human Skin Microbiome*. Cell, 2016. 165(4): p. 854-66.
21. Strube, M. L., et al., *A detailed investigation of the porcine skin and nose microbiome using universal and Staphylococcus specific primers*. Sci Rep, 2018. 8(1): p. 12751.
22. Martineau, F., et al., *Development of a PCR assay for identification of staphylococci at genus and species levels*. J Clin Microbiol, 2001. 39(7): p. 2541-7.
23. Fan, S. H., et al., *MpsAB is important for Staphylococcus aureus virulence and growth at atmospheric CO2 levels*. Nat Commun, 2019. 10(1): p. 3627.
24. Pallen, M. J. and B. W. Wren, *Bacterial pathogenomics*. Nature, 2007. 449(7164): p. 835-42.
25. Hazarika, R. A., et al., *Cutaneous infection associated with Staphylococcus hyicus in cattle*. Res Vet Sci, 1991. 50(3): p. 374-5.
26. Foster, A. P., *Staphylococcal skin disease in livestock*. Vet Dermatol, 2012. 23(4): p. 342-51, e63.
27. Ederveen, T. H. A. et al., *A generic workflow for Single Locus Sequence Typing (SLST) design and subspecies characterization of microbiota*. Sci Rep 2019, 9, 19834.
28. Ahle, C. M. et al., *Staphylococcus saccharolyticus: An Overlooked Human Skin Colonizer*. Microorganisms 2020, 8.

What is claimed is:

1. A method for amplifying the sequence or part of the sequence of a *Staphylococcus tuf* gene, wherein the method comprises (a) obtaining nucleic acid from bacteria of the genus *Staphylococcus;*

(b) amplifying the obtained nucleic acid with an oligonucleotide primer pair consisting of (i) a first primer comprising:

(i-a) the nucleotide sequence of SEQ ID NO:1; and (ii) a second primer comprising:

(ii-a) the nucleotide sequence of SEQ ID NO:2; and (c) optionally, sequencing the amplified nucleic acid.

2. The method of claim 1, wherein the nucleic acid is derived originates from bacteria that belong to a human microbiome.

3. The method of claim 2, wherein the human microbiome is a human skin microbiome.

4. The method of claim 1, wherein the nucleic acid is DNA.

5. The method of claim 1, wherein in (b) amplification is effected by a PCR, RT-PCR, real-time PCR or real-time RT-PCR reaction.

6. The method of claim 1, wherein (c) comprises NGS sequencing.

7. A method for identifying one or more *Staphylococcus* species and/or strains which are present in a biological sample, wherein the method comprises (a) obtaining nucleic acid from the biological sample;

(b) amplifying the obtained nucleic acid with an oligonucleotide primer pair consisting of (i) a first primer comprising:

(i-a) the nucleotide sequence of SEQ ID NO:1; and (ii) a second primer comprising:

(ii-a) the nucleotide sequence of SEQ ID NO:2;

(c) sequencing the amplified nucleic acid;

(d) comparing the sequences obtained in (c) with reference sequences from a plurality of *Staphylococcus* species and/or strains; and (e) assigning the sequences obtained in (c) to a *Staphylococcus* reference sequence, thereby identifying species and/or strains.

8. A method of amplifying the sequence or part of the sequence of a *Staphylococcus tuf* gene, wherein the method comprises contacting the sequence or part of the sequence of a *Staphylococcus tuf* gene with an oligonucleotide primer pair consisting of (i) a first primer comprising:

(i-a) the nucleotide sequence of SEQ ID NO:1; or (i-b) the complement of (i-a) and (ii) a second primer comprising:

(ii-a) the nucleotide sequence of SEQ ID NO:2; or (ii-b) the complement of (ii-a).

9. The method of claim 1, wherein the primers have a length of 19-70 nucleotides.

10. The method of claim 1, wherein the the primers have a length of 20-50 nucleotides.

11. The method of claim 1, wherein the the primers comprise sequencing adapters.

12. The method of claim 1, wherein (a) the first primer consists of the sequence of SEQ ID NO:1 or SEQ ID NO:3 and (b) the second primer consists of the sequence of SEQ ID NO:2 or SEQ ID NO:4.

* * * * *

SEQUENCE LISTING

```
<160> NUMBER OF SEQ ID NOS: 104

<210> SEQ ID NO 1
<211> LENGTH: 19
<212> TYPE: DNA
<213> ORGANISM: Artificial Sequence
<220> FEATURE:
<223> OTHER INFORMATION: Forward Primer

<400> SEQUENCE: 1

acaggccgtg ttgaacgtg                                                    19


<210> SEQ ID NO 2
<211> LENGTH: 20
<212> TYPE: DNA
<213> ORGANISM: Artificial Sequence
<220> FEATURE:
<223> OTHER INFORMATION: Reverse Primer

<400> SEQUENCE: 2

acagtacgtc caccttcacg                                                   20


<210> SEQ ID NO 3
<211> LENGTH: 52
<212> TYPE: DNA
<213> ORGANISM: Artificial Sequence
<220> FEATURE:
<223> OTHER INFORMATION: Forward Primer with Adapter

<400> SEQUENCE: 3

tcgtcggcag cgtcagatgt gtataagaga cagacaggcc gtgttgaacg tg               52


<210> SEQ ID NO 4
<211> LENGTH: 54
<212> TYPE: DNA
<213> ORGANISM: Artificial Sequence
<220> FEATURE:
<223> OTHER INFORMATION: Reverse Primer with Adapter

<400> SEQUENCE: 4

gtctcgtggg ctcggagatg tgtataagag acagacagta cgtccacctt cacg             54


<210> SEQ ID NO 5
<211> LENGTH: 467
<212> TYPE: DNA
<213> ORGANISM: Staphylococcus aureus
```

-continued

<220> FEATURE:
<223> OTHER INFORMATION: Strain B3-17D

<400> SEQUENCE: 5
acaggccgtg ttgaacgtgg tcaaatcaaa gttggtgaag aagttgaaat catcggttta 60
catgacacat ctaaaacaac tgttacaggt gttgaaatgt tccgtaaatt attagactac 120
gctgaagctg gtgacaacat tggtgcatta ttacgtggtg ttgctcgtga agacgtacaa 180
cgtggtcaag tattagctgc tcctggttca attacaccac atactgaatt taaagcagaa 240
gtatacgtat tatcaaaaga cgaaggtgga cgtcacactc cattcttctc aaactatcgt 300
ccacaattct atttccgtac tactgacgta actggtgttg ttcacttacc agaaggtact 360
gaaatggtaa tgcctggtga taacgttgaa atgacagtag aattaatcgc tccaatcgcg 420
attgaagacg gtactcgttt ctcaatccgc gaaggtggac gtactgt 467

<210> SEQ ID NO 6
<211> LENGTH: 467
<212> TYPE: DNA
<213> ORGANISM: Staphylococcus aureus
<220> FEATURE:
<223> OTHER INFORMATION: Strain FORC061

<400> SEQUENCE: 6
acaggccgtg ttgaacgtgg tcaaatcaaa gttggtgaag aagttgaaat catcggttta 60
catgacacat ctaaaacaac tgttacaggt gttgaaatgt tccgtaaatt attagactac 120
gctgaagctg gtgacaacat tggtgcatta ttacgtggtg ttgctcgtga agacgtacaa 180
cgtggtcaag tattagctgc tcctggttca attacaccac atactgaatt taaagcagaa 240
gtatacgtat tatcaaaaga cgaaggtgga cgtcacactc cattcttctc aaactatcgt 300
ccacaattct atttccgtac tactgacgta actggtgttg ttcacttacc agaaggaact 360
gaaatggtaa tgcctggtga taacgttgaa atgacagtag aattaatcgc tccaatcgcg 420
attgaagacg gtactcgttt ctcaatccgc gaaggtggac gtactgt 467

<210> SEQ ID NO 7
<211> LENGTH: 467
<212> TYPE: DNA
<213> ORGANISM: Staphylococcus aureus
<220> FEATURE:
<223> OTHER INFORMATION: Strain USA300

<400> SEQUENCE: 7
acaggccgtg ttgaacgtgg tcaaatcaaa gttggtgaag aagttgaaat catcggttta 60
catgacacat ctaaaacaac tgttacaggt gttgaaatgt tccgtaaatt attagactac 120
gctgaagctg gtgacaacat tggtgcatta ttacgtggtg ttgctcgtga agacgtacaa 180
cgtggtcaag tattagctgc tcctggttca attacaccac atactgaatt caaagcagaa 240
gtatacgtat tatcaaaaga cgaaggtgga cgtcacactc cattcttctc aaactatcgt 300
ccacaattct atttccgtac tactgacgta actggtgttg ttcacttacc agaaggtact 360
gaaatggtaa tgcctggtga taacgttgaa atgacagtag aattaatcgc tccaatcgcg 420
attgaagacg gtactcgttt ctcaatccgt gaaggtggac gtactgt 467

<210> SEQ ID NO 8
<211> LENGTH: 467
<212> TYPE: DNA
<213> ORGANISM: Staphylococcus aureus
<220> FEATURE:

-continued

<223> OTHER INFORMATION: Strain R50

<400> SEQUENCE: 8
acaggccgtg ttgaacgtgg tcaaatcaaa gttggtgaag aagttgaaat catcggttta 60
catgacacat ctaaaacaac tgttacaggt gttgaaatgt tccgtaaatt attagactac 120
gctgaagctg gtgacaacat tggtgcatta ttacgtggtg ttgctcgtga agacgtacaa 180
cgtggtcaag tattagctgc tcctggttca attacaccac atactgaatt caaagcagaa 240
gtatacgtat tatcaaaaga cgaaggcgga cgtcacactc cattcttctc aaactatcgt 300
ccacaattct atttccgtac tactgacgta actggtgttg ttcacttacc agaaggtact 360
gaaatggtaa tgcctggtga taacgttgaa atgacagtag aattaatcgc tccaatcgcg 420
attgaagacg gtactcgttt ctcaatccgt gaaggtggac gtactgt 467

<210> SEQ ID NO 9
<211> LENGTH: 467
<212> TYPE: DNA
<213> ORGANISM: Staphylococcus aureus
<220> FEATURE:
<223> OTHER INFORMATION: Strain 55-99-44

<400> SEQUENCE: 9
acaggccgtg ttgaacgtgg tcaaatcaaa gttggtgaag aagttgaaat catcggttta 60
catgaaacat ctaaaacaac tgttacaggt gttgaaatgt tccgtaaatt attagactac 120
gctgaagctg gtgacaacat tggtgcatta ttacgtggtg ttgctcgtga agacgtacaa 180
cgtggtcaag tattagctgc tcctggttca attacaccac atactgaatt caaagcagaa 240
gtatacgtat tatcaaaaga cgaaggtgga cgtcatactc cattcttctc aaactatcgt 300
ccacaattct atttccgtac tactgacgta actggtgttg ttcacttacc agaaggtact 360
gaaatggtaa tgcctggcga taacgttgaa atgacagtag aattaatcgc tccaatcgcg 420
attgaagacg gtactcgttt ctcaatccgt gaaggtggac gtactgt 467

<210> SEQ ID NO 10
<211> LENGTH: 872
<212> TYPE: DNA
<213> ORGANISM: Staphylococcus auricularis
<220> FEATURE:
<223> OTHER INFORMATION: Strain NCTC12101

<400> SEQUENCE: 10
acaggccgtg ttgaacgtgg tcaaatcaaa gtcggtgaag aagttgaaat catcggtatg 60
aaagacggtt cacaaaaaac aacagttact ggtgtagaaa tgttccgtaa attattagac 120
tacgctgaag ctggtgacaa catcggtgct ttattacgtg gtatttcacg tgaagaagta 180
caacgtggtc aagttttagc tgctcctggt tcaattacac cacacactaa attcactgca 240
gaagtttacg tattatctaa agatgaaggt ggacgtcaca ctccattctt ctctaactac 300
cgtccacaat tctatttccg tactactgac gtaacaggtg ttgttacttt accagaaggt 360
acagaaatgg taatgcctgg cgataacgtt aaaatggaag ttgcaggccg tgttgaacgt 420
ggtcaaatca aagtcggtga agaagttgaa atcatcggta tgaaagacgg ttcacaaaaa 480
acaacagtta ctggtgtaga aatgttccgt aaattattag actacgctga agctggtgac 540
aacatcggtg ctttattacg tggtatttca cgtgaagaag tacaacgtgg tcaagtttta 600
gctgctcctg gttcaattac accacacact aaattcactg cagaagttta cgtattatct 660
aaagatgaag gtggacgtca cactccattc ttctctaact accgtccaca attctatttc 720

-continued

```
cgtactactg acgtaacagg tgttgttact ttaccagaag gtacagaaat ggtaatgcct    780

ggcgataacg ttaaaatgga agttgaatta atttctccaa tcgctatcga agacggtact    840

cgtttctcaa ttcgtgaagg tggacgtact gt                                  872
```

```
<210> SEQ ID NO 11
<211> LENGTH: 467
<212> TYPE: DNA
<213> ORGANISM: Staphylococcus capitis
<220> FEATURE:
<223> OTHER INFORMATION: Strain AYP1020

<400> SEQUENCE: 11

acaggccgtg ttgaacgtgg tcaaatcaaa gttggtgaag aagttgaaat catcggtatc     60

cacgaaactt ctaaaacaac tgttactggt gtagaaatgt tccgtaaatt attagactac    120

gctgaagctg gtgacaacat cggtgcttta ttacgtggtg ttgctcgtga agacgtacaa    180

cgtggtcaag tattagctgc tcctggttca atcacaccac acactaaatt caaagcggaa    240

gtttacgttt tatctaaaga cgaaggtgga cgtcacactc cattcttcag taactaccgc    300

ccacaattct atttccgtac tactgacgta actggtgttg ttaacttacc agaaggtact    360

gaaatggtta tgcctggcga caacgttgaa atgacagttg aattaatcgc tcctatcgct    420

attgaagacg gtactcgttt ctcaatccgt gaaggtggac gtactgt                  467
```

```
<210> SEQ ID NO 12
<211> LENGTH: 467
<212> TYPE: DNA
<213> ORGANISM: Staphylococcus caprae
<220> FEATURE:
<223> OTHER INFORMATION: Strain SNUC4023

<400> SEQUENCE: 12

acaggccgtg ttgaacgtgg tcaaatcaaa gttggtgaag aagttgaaat catcggtatc     60

cacgaaactt ctaaaacaac tgttactggt gtagaaatgt tccgtaaatt attagactac    120

gctgaagctg gtgacaacat cggtgcatta ttacgtggtg ttgctcgtga agacgtacaa    180

cgtggtcaag tattagctgc tcctggttca atcacaccac acactaaatt caaagctgaa    240

gtatacgttt tatctaaaga cgaaggtgga cgtcacactc cattcttcag taactaccgc    300

ccacaattct atttccgtac tactgacgta actggtgttg taaacttacc agaaggtact    360

gaaatggtta tgcctggcga caacgttgaa atgacagttg aattaatcgc tcctatcgca    420

attgaagacg gtactcgttt ctcaatccgt gaaggtggac gtactgt                  467
```

```
<210> SEQ ID NO 13
<211> LENGTH: 467
<212> TYPE: DNA
<213> ORGANISM: Staphylococcus carnosus
<220> FEATURE:
<223> OTHER INFORMATION: Strain DSM20501S

<400> SEQUENCE: 13

acaggccgtg ttgaacgtgg tcaaatcaaa gttggtgaag aagttgaaat catcggttta     60

cacgacactt ctaaaacaac tgttactggt gtagaaatgt tccgtaaatt attagactac    120

gctgaagctg gtgacaacat cggtgcatta ttacgtggtg ttgctcgtga agacgtacaa    180

cgtggtcaag tattagctgc tccaggttca atcacacctc acactaaatt caaagcagac    240

gtatacgttt tatctaaaga cgaaggtgga cgtcacactc cattcttctc aaactatcgt    300
```

```
ccacaattct atttccgtac tactgacgta actggtgttg ttaacttacc agaaggtaca    360

gaaatggtta tgcctggcga caacgttgaa atgacagtag aattaatcgc tcctatcgca    420

attgaagacg gtactcgttt ctcaatccgt gaaggtggac gtactgt                  467


<210> SEQ ID NO 14
<211> LENGTH: 470
<212> TYPE: DNA
<213> ORGANISM: Staphylococcus carnosus
<220> FEATURE:
<223> OTHER INFORMATION: Strain LTH7013

<400> SEQUENCE: 14

acaggccgtg ttgaacgtgg tcaaatcaaa gtcggtgaag aagttgaaat catcggtatc     60

actgaagaaa gcatgaaaac aacagttaca ggtgtagaaa tgttccgtaa attattagac    120

tacgctgaag ctggtgacaa cattggtgct ttattacgtg gtgttgcacg tgaagacgta    180

caacgtggac aagtattagc agctcctggc tctattactc cacacactaa atttaaagct    240

gatgtttatg ttttatctaa agatgaaggt ggacgtcata ctccattctt cactaactac    300

cgcccacaat tctacttccg tactactgac gtaactggtg ttgttaactt accagaaggt    360

actgaaatgg ttatgcctgg cgataacgta gaaatgactg ttgaattgat tgctccaatc    420

gcaatcgaag acggtactcg tttctctatc cgtgaaggtg gacgtactgt               470


<210> SEQ ID NO 15
<211> LENGTH: 470
<212> TYPE: DNA
<213> ORGANISM: Staphylococcus chromogenes
<220> FEATURE:
<223> OTHER INFORMATION: Strain 117

<400> SEQUENCE: 15

actggccgtg ttgaacgtgg tcaaatcaaa gttggtgaag aagttgaaat catcggttta     60

tctgaagaat cttctaaaac aactgttact ggtgtagaaa tgttccgtaa gttattagac    120

tacgctgaag ctggtgacaa cattggtgct ttattacgtg gtgttgctcg tgaagacgta    180

caacgtggtc aagtattagc tgctcctggt tcaatcacac cacacacaaa atttaaagct    240

gaagtatacg ttttatcaaa agacgaaggt ggacgtcaca ctccattctt ctctaactac    300

cgcccacaat tctatttccg tactactgac gtaactggcg ttgttaactt accagaaggt    360

actgaaatgg ttatgcctgg cgataacgta gaaatggacg ttgagttaat ttctccaatc    420

gctatcgaag acggtactcg tttctcaatc cgtgaaggtg gacgtactgt               470


<210> SEQ ID NO 16
<211> LENGTH: 470
<212> TYPE: DNA
<213> ORGANISM: Staphylococcus chromogenes
<220> FEATURE:
<223> OTHER INFORMATION: Strain SNUC1139

<400> SEQUENCE: 16

actggccgtg ttgaacgtgg tcaaatcaaa gttggtgaag aagttgaaat catcggttta     60

tctgaagaat cttctaaaac aactgttact ggtgtagaaa tgttccgtaa gttattagac    120

tacgctgaag ctggtgacaa catcggtgct ttattacgtg gtgttgctcg tgaagacgta    180

caacgtggtc aagtattagc tgctcctggt tcaatcacac cacacacaaa atttaaagct    240

gaagtatacg ttttatcaaa agacgaaggt ggacgtcaca ctccattctt ctctaactac    300

cgcccacaat tctatttccg tactactgac gtaactggcg ttgttaactt accagaaggt    360
```

-continued

```
actgaaatgg ttatgcctgg cgataacgta gaaatggacg ttgagttaat ttctccaatc    420

gctatcgaag acggtactcg tttctcaatc cgtgaaggtg gacgtactgt               470


<210> SEQ ID NO 17
<211> LENGTH: 470
<212> TYPE: DNA
<213> ORGANISM: Staphylococcus chromogenes
<220> FEATURE:
<223> OTHER INFORMATION: Strain SNUC-126

<400> SEQUENCE: 17

actggccgtg ttgaacgtgg tcaaatcaaa gttggtgaag aagttgaaat catcggttta     60

actgaagaat cttctaaaac aactgttact ggtgtagaaa tgttccgtaa gttattagac    120

tacgctgaag ctggtgacaa cattggtgct ttattacgtg gtgttgctcg tgaagacgtt    180

caacgtggtc aagtattagc tgctcctggt tcaatcacac cacacacaaa atttaaagct    240

gaagtatacg ttttatcaaa agacgaaggt ggacgtcaca ctccattctt ctctaactac    300

cgcccacaat tctatttccg tactactgac gtaactggcg ttgttaactt accagaaggt    360

actgaaatgg ttatgcctgg cgataacgta gaaatggacg ttgagttaat ttctccaatc    420

gctatcgaag acggtactcg tttctcaatc cgtgaaggtg gacgtactgt               470


<210> SEQ ID NO 18
<211> LENGTH: 470
<212> TYPE: DNA
<213> ORGANISM: Staphylococcus chromogenes
<220> FEATURE:
<223> OTHER INFORMATION: Strain SNUC-1379

<400> SEQUENCE: 18

actggtcgtg ttgaacgtgg tcaaatcaaa gttggtgaag aagttgaaat catcggttta     60

actgaagaat cttctaaaac aactgttact ggtgtagaaa tgttccgtaa gttattagac    120

tacgctgaag ctggtgacaa cattggtgct ttattacgtg gtgttgctcg tgaagacgta    180

caacgtggtc aagtattagc tgctcctggt tcaatcacac cacacacaaa atttaaagct    240

gaagtatacg ttttatcaaa agacgaaggt ggacgtcaca ctccattctt ctctaactac    300

cgcccacagt tctatttccg tactactgac gtaactggcg ttgttaactt accagaaggt    360

actgaaatgg ttatgcctgg cgataacgta gaaatggacg ttgagttaat ttctccaatc    420

gctatcgaag acggtactcg tttctcaatc cgtgaaggtg gacgtactgt               470


<210> SEQ ID NO 19
<211> LENGTH: 470
<212> TYPE: DNA
<213> ORGANISM: Staphylococcus chromogenes
<220> FEATURE:
<223> OTHER INFORMATION: Strain 532

<400> SEQUENCE: 19

acaggccgtg ttgaacgtgg tcaaatcaaa gtcggtgaag aagttgaaat catcggtatg     60

caagaagaat caagcaaaac aactgttact ggtgtagaaa tgttccgtaa attattagac    120

tatgctgaag ctggtgacaa cattggtgcg ttattacgtg gtgttgcacg tgaagacatc    180

caacgtggtc aagttttagc tgctcctggt tcaattacac cacatacaaa gtttaaagcg    240

gaagtttacg ttttatctaa agatgaaggt ggacgtcata ctccattctt cagtaactac    300

cgcccacaat tctatttccg tactactgac gtaacaggcg ttgttacttt accagaaggt    360
```

actgaaatgg ttatgcctgg cgacaatgtt gaaatggaag ttgaactaat ttctccaatc 420
gctatcgaag acggtacacg tttctctatc cgtgaaggtg gacgtactgt 470

<210> SEQ ID NO 20
<211> LENGTH: 470
<212> TYPE: DNA
<213> ORGANISM: Staphylococcus cohnii
<220> FEATURE:
<223> OTHER INFORMATION: Strain SNUC-3213

<400> SEQUENCE: 20
acaggccgtg ttgaacgtgg tcaaatcaaa gtcggtgaag aagttgaaat catcggtatg 60
caagaagatt caagcaaaac aactgttact ggtgtagaaa tgttccgtaa attattagac 120
tacgctgaag ctggtgacaa cattggtgcg ttattacgtg gtgttgcacg tgaagacatc 180
caacgtggtc aagttttagc tgctcctggt tcaattacac cacatacaaa ctttaaagcg 240
gaagtttacg ttttatcaaa agatgaaggt ggccgtcata cgccgttctt cagtaactac 300
cgcccacaat tctatttccg tactactgac gtaacaggtg ttgttacttt accagaaggt 360
actgaaatgg ttatgcctgg tgacaacgta gaaatggaag ttgaattaat ttctccaatc 420
gctatcgaag acggtacacg tttctctatc cgtgaaggtg gacgtactgt 470

<210> SEQ ID NO 21
<211> LENGTH: 470
<212> TYPE: DNA
<213> ORGANISM: Staphylococcus cohnii
<220> FEATURE:
<223> OTHER INFORMATION: Strain SNUC-1120

<400> SEQUENCE: 21
acaggccgtg ttgaacgtgg tcaaatcaaa gtcggtgaag aagttgaaat catcggtatg 60
caagaagatt caagcaaaac aactgttact ggtgtagaaa tgttccgtaa attattagac 120
tacgctgaag ctggtgacaa cattggtgcg ttattacgtg gtgttgcacg tgaagacatc 180
caacgtggtc aagttatagc tgctcctggt tcaattacac cacatacaaa ctttaaagcg 240
gaagtttacg ttttatcaaa agatgaaggc ggccgtcata cgccattctt cagtaactac 300
cgcccacaat tctatttccg tactactgac gtaacaggtg ttgttacttt accagaaggt 360
actgaaatgg ttatgcctgg cgacaacgta gaaatggaag ttgaattaat ttctccaatc 420
gctatcgaag acggtacacg tttctctatc cgtgaaggtg gacgtactgt 470

<210> SEQ ID NO 22
<211> LENGTH: 471
<212> TYPE: DNA
<213> ORGANISM: Staphylococcus condimenti
<220> FEATURE:
<223> OTHER INFORMATION: Strain DSM11674

<400> SEQUENCE: 22
acaggccgtg ttgaacgtgg tcaaatcaaa gtcggtgaag aagttgaaat catcggtatc 60
actgaagaaa gcatgaaaac aacagttaca ggtgtagaaa tgttccgtaa attattagac 120
tacgctgaag ctggtgacaa cattggtgct ttattacgtg gtgttgcacg tgaagacgta 180
caacgtggac aagtattagc agctcctggt tctattactc cacacactaa atttaaagct 240
gatgtttatg ttttatctaa agatgaaggt ggacgtcata ctccattctt cactaactac 300
cgcccacaat tctacttccg tactactgac gtaactggtg ttgttaactt accagaaggt 360
actgaaatgg ttatgcctgg cgataacgta gaaatgactg ttgaattgat ttctccaatc 420
gctatcgaag acggtactcg tttctctatc cgtgaaggtg gacgtactgt t 471

<210> SEQ ID NO 23
<211> LENGTH: 470
<212> TYPE: DNA
<213> ORGANISM: Staphylococcus delphini
<220> FEATURE:
<223> OTHER INFORMATION: Strain DSM20771

<400> SEQUENCE: 23
actggtcgtg ttgaacgtgg tcaaatcaaa gttggtgacg aagttgaaat catcggttta 60
actgaagaat cttctaaaac aactgttact ggtgtagaaa tgttccgtaa gttattagac 120
tacgctgaag ctggtgacaa cattggtgct ttattacgtg gtgttgcacg tgaagacatc 180
aaccgtggtc aagtattagc ggctcctggt tcaatcacac cacacacaaa atttaaagcg 240
gaagtttacg tattatcaaa agacgaaggt ggtcgtcata caccattctt ctctaactac 300
cgcccacaat tctatttccg tactactgac gtaactggtg ttgtaaactt accagaaggt 360
actgaaatgg taatgcctgg cgataacgtt gaaatggaag ttgaattaat ttctccaatc 420
gctatcgaag acggtactcg tttttcaatt cgtgaaggtg gacgtactgt 470

<210> SEQ ID NO 24
<211> LENGTH: 470
<212> TYPE: DNA
<213> ORGANISM: Staphylococcus delphini
<220> FEATURE:
<223> OTHER INFORMATION: Strain 14S03311-1

<400> SEQUENCE: 24
actggtcgtg ttgaacgtgg tcaaatcaaa gttggtgacg aagtagaaat catcggttta 60
actgaagaat cttctaaaac aactgttact ggtgtagaaa tgttccgtaa gttattagac 120
tacgctgaag ctggtgacaa cattggtgct ttattacgtg gtgttgcacg tgaagacatc 180
aaccgtggtc aagtattagc ggctcctggt tcaatcacac cacacacaaa atttaaagcg 240
gaagtttacg tattatcaaa agacgaaggt ggtcgtcata caccattctt ctctaactac 300
cgcccacaat tctatttccg tactactgac gtaactggtg ttgtaaactt accagaaggt 360
actgaaatgg taatgcctgg cgataacgtt gaaatggaag ttgaattaat ttctccaatc 420
gctatcgaag acggtactcg tttctcaatt cgtgaaggtg gacgtactgt 470

<210> SEQ ID NO 25
<211> LENGTH: 470
<212> TYPE: DNA
<213> ORGANISM: Staphylococcus delphini
<220> FEATURE:
<223> OTHER INFORMATION: Strain 215100905101-2

<400> SEQUENCE: 25
actggtcgtg ttgaacgtgg tcaaatcaaa gttggtgacg aagttgaaat catcggttta 60
actgaagaat cttctaaaac aactgttact ggtgtagaaa tgttccgtaa gttattagac 120
tacgctgaag ctggtgacaa cattggtgct ttattacgtg gtgttgcacg tgaagacatc 180
aaccgtggtc aagtattagc ggctcctggt tcaatcacac cacacacaaa atttaaagcg 240
gaagtttacg tattatcaaa agacgaaggt ggtcgtcata caccattctt ctctaactac 300
cgcccacaat tctatttccg tactactgac gtaactggtg ttgtaaactt accagaaggt 360
actgaaatgg taatgcctgg cgataacgtt gaaatggaag ttgaattaat ttctccaatc 420
gctatcgaag acggtactcg tttctcaatt cgtgaaggtg gacgtactgt 470

<210> SEQ ID NO 26
<211> LENGTH: 467
<212> TYPE: DNA
<213> ORGANISM: Staphylococcus devriesei
<220> FEATURE:
<223> OTHER INFORMATION: Strain SNUC-1409

<400> SEQUENCE: 26
acaggccgtg ttgaacgtgg tcaaatcaaa gttggtgaag aagttgaaat catcggatta 60
cacgacactt ctaaaacaac tgttactggt gtagaaatgt tccgtaaatt attagactat 120
gctgaagctg gtgacaacat cggtgcatta ttacgtggtg ttgctcgtga agacgtacaa 180
cgtggacaag tattagctgc tccaggttca attactcctc atacaaaatt caaagctgac 240
gtatacgttt tatctaaaga cgaaggtgga cgtcacactc cattcttctc aaactatcgt 300
ccacaattct atttccgtac tactgacgta actggtgtag ttaacttacc agaaggtact 360
gaaatggtta tgcctggcga caacgttgaa atgacagtag aattaatcgc tcctatcgct 420
attgaagacg gtactcgttt ctcaatccgt gaaggtggac gtactgt 467

<210> SEQ ID NO 27
<211> LENGTH: 467
<212> TYPE: DNA
<213> ORGANISM: Staphylococcus devriesei
<220> FEATURE:
<223> OTHER INFORMATION: Strain SNUC-1156

<400> SEQUENCE: 27
acaggccgtg ttgaacgtgg tcaaatcaaa gttggtgaag aagttgaaat catcggatta 60
cacgagactt ctaaaacaac tgttactggt gtagaaatgt tccgtaaatt attagactat 120
gctgaagctg gtgacaacat cggtgcatta ttacgtggtg ttgctcgtga agacgtacaa 180
cgtggacaag tattagctgc tccaggttca attactcctc atacaaaatt caaagctgac 240
gtatacgttt tatctaaaga cgaaggtgga cgtcacactc cattcttctc aaactatcgt 300
ccacaattct atttccgtac tactgacgta actggtgtag ttaacttacc agaaggtact 360
gaaatggtta tgcctggcga caacgttgaa atgacagtag aattaatcgc tcctatcgct 420
attgaagacg gtactcgttt ctcaatccgt gaaggtggac gtactgt 467

<210> SEQ ID NO 28
<211> LENGTH: 470
<212> TYPE: DNA
<213> ORGANISM: Staphylococcus edaphicus
<220> FEATURE:
<223> OTHER INFORMATION: Strain CCM-8730

<400> SEQUENCE: 28
acaggccgtg ttgaacgtgg tcaaatcaaa gtcggtgaag aagttgaaat cattggtatg 60
caagaagatt caagcaaaac aactgttact ggtgtagaaa tgttccgtaa attattagac 120
tacgctgaag ctggtgacaa cattggtgca ttattacgtg gtgtttcacg tgatgacgta 180
caacgtggtc aagttttagc tgctcctggt actattacac cacatacaaa attcaaagcg 240
gatgtttacg ttttatctaa agatgaaggt ggccgtcata caccattctt cactaactac 300
cgcccacaat tctatttccg tactactgac gtaactggtg ttgttaactt accagaaggt 360
actgaaatgg ttatgcctgg cgataacgtt gaaatggaag ttgaattaat ttctccaatc 420
gctattgaag acggtacacg tttctctatc cgtgaaggtg gacgtactgt 470

<210> SEQ ID NO 29
<211> LENGTH: 467
<212> TYPE: DNA
<213> ORGANISM: Staphylococcus epidermidis
<220> FEATURE:
<223> OTHER INFORMATION: Strain ATCC-12228

<400> SEQUENCE: 29
acaggccgtg ttgaacgtgg tcaaatcaaa gttggtgaag aagttgaaat catcggtatg 60
cacgaaactt ctaaaacaac tgttactggt gtagaaatgt tccgtaaatt attagactac 120
gctgaagctg gtgacaacat cggtgcttta ttacgtggtg ttgcacgtga agacgtacaa 180
cgtggtcaag tattagctgc tcctggttct attacaccac acacaaaatt caaagctgaa 240
gtatacgtat tatctaaaga tgaaggtgga cgtcacactc cattcttcac taactatcgc 300
ccacaattct atttccgtac tactgacgta actggtgttg taaacttacc agaaggtaca 360
gaaatggtta tgcctggcga caacgttgaa atgacagttg aattaatcgc tccaatcgct 420
atcgaagacg gaactcgttt ctcaattcgt gaaggtggac gtactgt 467

<210> SEQ ID NO 30
<211> LENGTH: 467
<212> TYPE: DNA
<213> ORGANISM: Staphylococcus epidermidis
<220> FEATURE:
<223> OTHER INFORMATION: Strain SE95

<400> SEQUENCE: 30
acaggccgtg ttgaacgtgg tcaaatcaaa gttggtgaag aagttgaaat catcggtatg 60
cacgaaactt ctaaaacaac tgttactggt gtagaaatgt tccgtaaatt attagactac 120
gctgaagctg gtgacaacat cggtgcttta ttacgtggtg ttgcacgtga agacgtacaa 180
cgtggtcaag tattagctgc tcctggttct attacaccac acacaaaatt caaagctgaa 240
gtatacgtat tatctaaaga tgaaggtgga cgtcacactc cattcttcac taactatcgc 300
ccacaattct atttccgtac tactgacgta actggtgttg taaacttacc agaaggtaca 360
gaaatggtta tgcctggcga taacgttgaa atgacagttg aattaatcgc tccaatcgct 420
atcgaagacg gaactcgttt ctcaattcgt gaaggtggac gtactgt 467

<210> SEQ ID NO 31
<211> LENGTH: 467
<212> TYPE: DNA
<213> ORGANISM: Staphylococcus epidermidis
<220> FEATURE:
<223> OTHER INFORMATION: SEI

<400> SEQUENCE: 31
acaggccgtg ttgaacgtgg tcaaatcaaa gttggtgaag aagttgaaat catcggtatg 60
cacgaaactt ctaaaacaac tgttactggt gtagaaatgt tccgtaaatt attagactac 120
gctgaagctg gtgacaacat cggtgcttta ttacgtggtg ttgcacgtga agacgtacaa 180
cgtggtcaag tattagctgc tcctggttct attacaccac acacaaaatt caaagctgaa 240
gtatacgtat tatctaaaga tgaaggtgga cgtcacactc cattcttcac taactatcgc 300
ccacaattct atttccgtac tactgacgta actggtgttg taaacttacc agaaggtaca 360
gaaatggtta tgcctggtga caacgttgaa atgacagttg aattaatcgc tccaatcgct 420
atcgaagacg gaactcgttt ctcaattcgt gaaggtggac gtactgt 467

<210> SEQ ID NO 32
<211> LENGTH: 467
<212> TYPE: DNA
<213> ORGANISM: Staphylococcus epidermidis
<220> FEATURE:
<223> OTHER INFORMATION: Strain FDAARGOS-529

<400> SEQUENCE: 32
acaggccgtg ttgaacgtgg tcaaatcaaa gttggtgaag aagttgaaat catcggtatg 60
catgaaactt ctaaaacaac tgttactggt gtagaaatgt tccgtaagtt attagactac 120
gctgaagctg gtgacaacat cggtgcttta ttacgtggtg ttgcacgtga agacgtacaa 180
cgtggtcaag tattagctgc tcctggttct attacaccac acacaaaatt caaagctgaa 240
gtatacgtat tatctaaaga tgaaggtgga cgtcacactc cattcttcac taactatcgc 300
ccacaattct atttccgtac tactgacgta actggtgttg taaacttacc agaaggtaca 360
gaaatggtta tgcctggcga caacgttgaa atgacagttg aattaatcgc tccaatcgct 420
atcgaagacg gaactcgttt ctcaattcgt gaaggtggac gtactgt 467

<210> SEQ ID NO 33
<211> LENGTH: 470
<212> TYPE: DNA
<213> ORGANISM: Staphylococcus equorum
<220> FEATURE:
<223> OTHER INFORMATION: Strain 900-4

<400> SEQUENCE: 33
acaggccgtg ttgaacgtgg tcaaatcaaa gtcggtgctg aaattgaaat catcggtatg 60
caagaggaat caactaagac aactgttaca ggtgttgaaa tgttccgtaa attactagac 120
tacgctgaag ctggcgacaa cattggtgct ttattacgtg gtgtatcacg tgatgacatc 180
tctcgtggac aagttttagc tgcgcctggt actattacac cgcatactaa cttcaaagca 240
gacgtttatg ttttatcaaa agaagaaggt ggacgtcata ctccattctt cactaactac 300
cgtccgcaat tctatttccg tactactgac gtaacaggcg ttgttacttt accagaaggt 360
actgaaatgg ttatgcctgg cgataacgtt gaaatgcaag ttgaattgat ttcaccaatc 420
gctatcgaag atggtactcg tttctctatc cgtgaaggtg gacgtactgt 470

<210> SEQ ID NO 34
<211> LENGTH: 470
<212> TYPE: DNA
<213> ORGANISM: Staphylococcus equorum
<220> FEATURE:
<223> OTHER INFORMATION: Strain SNUC-284

<400> SEQUENCE: 34
acaggccgtg ttgaacgtgg tcaaatcaaa gtcggtgctg aaattgaaat catcggtatg 60
caagaggaat caactaagac aactgttaca ggtgttgaaa tgttccgtaa attactagac 120
tacgctgaag ctggcgacaa cattggtgct ttattacgtg gtgtatcacg tgatgacatt 180
tctcgtggac aagttttagc tgcgcctggt actattacac cgcatactaa cttcaaagca 240
gacgtttatg ttttatcaaa agaagaaggt ggacgtcata ctccattctt cactaactac 300
cgtccgcaat tctatttccg tactactgac gtaacaggcg ttgttacttt accagaaggt 360
actgaaatgg ttatgcctgg cgataacgtt gaaatgcaag ttgaattgat ttcaccaatc 420
gctatcgaag atggtactcg tttctctatc cgtgaaggtg gacgtactgt 470

```
<210> SEQ ID NO 35
<211> LENGTH: 470
<212> TYPE: DNA
<213> ORGANISM: Staphylococcus equorum
<220> FEATURE:
<223> OTHER INFORMATION: Strain BC9

<400> SEQUENCE: 35

acaggccgtg ttgaacgtgg tcaaatcaaa gtcggcgctg aaattgaaat catcggtatg     60

caagaggaat caactaaaac aactgttaca ggtgttgaaa tgttccgtaa attactagac    120

tacgctgaag ctggcgacaa cattggtgct ttattacgtg gtgtatcacg tgatgacatc    180

tctcgtggac aagttttagc tgcacctggt actattacac cgcatactaa cttcaaagca    240

gacgtttatg ttttatcaaa agaagaaggt ggacgtcata ctccattctt cactaactac    300

cgtccgcaat tctatttccg tactactgac gtaacaggtg ttgttacttt accagaaggt    360

actgaaatgg ttatgcctgg cgataacgtt gaaatgcaag ttgaattgat ttcaccaatc    420

gctatcgaag atggtactcg tttctctatc cgtgaaggtg gacgtactgt               470


<210> SEQ ID NO 36
<211> LENGTH: 470
<212> TYPE: DNA
<213> ORGANISM: Staphylococcus equorum
<220> FEATURE:
<223> OTHER INFORMATION: Strain SNUC-476

<400> SEQUENCE: 36

acaggccgtg ttgaacgtgg tcaaatcaaa gtcggtgctg aaattgaaat catcggtatg     60

caagaggaat caactaaaac aactgttaca ggtgttgaaa tgttccgtaa attattagac    120

tacgctgaag ctggcgacaa cattggtgct ttattacgtg gtgtatcacg tgatgacatc    180

tctcgtggac aagttttagc tgcgcctggt actattacac cgcatactaa cttcaaagca    240

gacgtttatg ttttatcaaa agaagaaggt ggacgtcata ctccattctt cactaactac    300

cgtccgcaat tctatttccg tactactgac gtaactggcg ttgttagttt accagaaggt    360

actgaaatgg ttatgcctgg cgataacgtt gaaatgcaag ttgaattgat ttcaccaatc    420

gctatcgaag atggtactcg tttctctatc cgtgaaggtg gacgtactgt               470


<210> SEQ ID NO 37
<211> LENGTH: 470
<212> TYPE: DNA
<213> ORGANISM: Staphylococcus felis
<220> FEATURE:
<223> OTHER INFORMATION: Strain F1-k127-55

<400> SEQUENCE: 37

acaggccgtg ttgaacgtgg tcaaatcaaa gttggtgaag aagttgaaat catcggttta     60

actgaacaat cttctaaaac aactgttact ggtgtagaaa tgttccgtaa gttattagac    120

tacgctgaag ctggtgacaa catcggtgca ttattacgtg gtgttgctcg tgaagacatc    180

aaccgtggac aagttttagc tgctcctggt tcaatcacac cacacacaaa atttaaagca    240

gaagtttacg tattatcaaa agacgaaggt ggacgtcaca cgccattctt ctctaactac    300

cgcccacaat tctatttccg tactactgac gtaactggtg tagttaactt accagaaggt    360

acagaaatgg ttatgcctgg cgataacgtt gaaatggaag ttgaattaat ttctccaatc    420

gctatcgaag acggtacacg tttctcaatc cgtgaaggtg gacgtactgt               470


<210> SEQ ID NO 38
```

-continued

<211> LENGTH: 470
<212> TYPE: DNA
<213> ORGANISM: Staphylococcus felis
<220> FEATURE:
<223> OTHER INFORMATION: Strain F27-k127-298

<400> SEQUENCE: 38

```
acaggccgtg ttgaacgtgg tcaaatcaaa gttggtgaag aagttgaaat catcggttta     60

actgaacaat cttctaaaac aactgttact ggtgtagaaa tgttccgtaa gttattagac    120

tacgctgaag ctggtgacaa catcggtgca ttattacgtg gtgttgctcg tgaagacatc    180

aaccgtggac aagttttagc tgctcctggt tcaatcacac cacacacaaa atttaaagct    240

gaagtttacg tattatcaaa agacgaaggt ggacgtcaca cgccattctt ctctaactac    300

cgcccacaat tctatttccg tactactgac gtaactggtg tagttaactt accagaaggt    360

acagaaatgg ttatgcctgg cgataacgtt gaaatggaag ttgaattaat ttctccaatc    420

gctatcgaag acggtacacg tttctcaatc cgtgaaggtg gacgtactgt               470
```

<210> SEQ ID NO 39
<211> LENGTH: 470
<212> TYPE: DNA
<213> ORGANISM: Staphylococcus felis
<220> FEATURE:
<223> OTHER INFORMATION: Strain F8-k127-533

<400> SEQUENCE: 39

```
acaggccgtg ttgaacgtgg tcaaatcaaa gttggtgaag aagttgaaat catcggttta     60

actgaacaat cttctaaaac aactgttact ggtgtagaaa tgttccgtaa gttattagac    120

tacgctgaag ctggtgacaa catcggtgca ttattacgtg gtgttgctcg tgaagacatc    180

aaccgtggac aagttttagc tgctcctggt tcaatcacac cacacacaaa atttaaagct    240

gaagtttacg tattatcaaa agatgaaggt ggacgtcata cgccattctt ctctaactac    300

cgcccacaat tctatttccg tactactgac gtaactggtg tagttaactt accagaaggt    360

acagaaatgg ttatgcctgg cgataacgtt gaaatggaag ttgaattaat ttctccaatc    420

gctatcgaag acggtacacg tttctcaatc cgtgaaggtg gacgtactgt               470
```

<210> SEQ ID NO 40
<211> LENGTH: 470
<212> TYPE: DNA
<213> ORGANISM: Staphylococcus felis
<220> FEATURE:
<223> OTHER INFORMATION: Strain F29-k127-272

<400> SEQUENCE: 40

```
acaggccgtg ttgaacgtgg tcaaatcaaa gttggtgaag aagttgaaat catcggttta     60

actgaacaat cttctaaaac aactgttact ggtgtagaaa tgttccgtaa gttattagac    120

tacgctgaag ctggtgacaa catcggtgca ttattacgtg gtgttgctcg tgaagacatc    180

aaccgtggac aagttttagc tgctcctggt tcaatcacac cacacacaaa atttaaagct    240

gaagtttacg tattatcaaa agacgaaggt ggacgtcata cgccattctt ctctaactac    300

cgcccacaat tctatttccg tactactgac gtaactggtg tagttaactt accagaaggt    360

acagaaatgg ttatgcctgg cgataacgtt gaaatggaag ttgaattaat ttctccaatc    420

gctatcgaag acggtacacg tttctcaatc cgtgaaggtg gacgtactgt               470
```

<210> SEQ ID NO 41
<211> LENGTH: 470

-continued

<212> TYPE: DNA
<213> ORGANISM: Staphylococcus fleurettii
<220> FEATURE:
<223> OTHER INFORMATION: Strain DSM-13212

<400> SEQUENCE: 41
actggtcgtg ttgaacgtgg tcaaatcaaa gttggtgaag aagttgaaat catcggttta 60
gctgaagaat cttctaaaac aactgttact ggtgtagaaa tgttccgtaa attattagac 120
tacgctgaag ctggtgacaa cattggtgct ttattacgtg gtgttgcacg tgaagacatc 180
aaccgtggtc aagtattagc tgctcctggt tcaattacac cacacacaaa gtttaaagca 240
gaagtttacg tattatctaa agacgaaggt ggtcgtcaca caccattctt ctctaactac 300
cgcccacaat tctatttccg tactactgac gtaactggcg ttgttcactt accagaaggt 360
actgaaatgg ttatgcctgg cgataacgtt gaaatggaag ttgaattaat ttcaccaatc 420
gctatcgaag acggtactcg tttctcaatt cgtgaaggtg gacgtactgt 470

<210> SEQ ID NO 42
<211> LENGTH: 470
<212> TYPE: DNA
<213> ORGANISM: Staphylococcus fleurettii
<220> FEATURE:
<223> OTHER INFORMATION: Strain NCTC13829

<400> SEQUENCE: 42
acaggccgtg ttgaacgtgg tcaaatcaaa gttggtgaag agattgaaat catcggttta 60
actgaagaat cttctaaaac aactgtaact ggtgttgaaa tgttccgtaa attattagac 120
ttcgctgaag ctggagataa catcggtgct ttattacgtg gtgttgctcg tgaagacgtt 180
aaccgtggtc aagtattagc taaaccaggt tcaatcactc ctcacactaa attcaaagcg 240
gaagtttatg tattatcaaa agaagaaggt ggacgtcata ctccattctt cactaactac 300
cgcccacaat tctatttccg tacaactgac gtaactggtg tagtaaactt accagaaggc 360
attgaaatgg ttatgcctgg cgacaacgtt gaaatggacg ttgaattaat ttcaccaatc 420
gctattgaag acggtactcg tttctcaatt cgtgaaggtg gacgtacagt 470

<210> SEQ ID NO 43
<211> LENGTH: 470
<212> TYPE: DNA
<213> ORGANISM: Staphylococcus gallinarum
<220> FEATURE:
<223> OTHER INFORMATION: Strain DSM20610

<400> SEQUENCE: 43
acaggccgtg ttgaacgtgg tcaaatcaaa gtcggtgaag aaatcgaaat catcggtatg 60
caagaagaat caagcaaaac aactgttact ggtgtagaaa tgttccgtaa gttattagac 120
tacgctgaag ctggtgacaa cattggtgca ttattacgtg gtgtttcacg tgaagatgtt 180
caacgtggtc aagttttagc tgctcctggt actattacac cacatacaaa attcaaagcg 240
gaagtttacg ttttatctaa agacgaaggt ggacgtcata ctccattctt cactaactac 300
cgcccacaat tctatttccg tactactgac gtaactggtg ttgttaactt accagaaggt 360
actgaaatgg ttatgcctgg cgataacgtt gaaatgatcg ttgaattaat ttctccaatc 420
gctatcgaag acggtactcg tttctctatc cgtgaaggtg gacgtactgt 470

<210> SEQ ID NO 44
<211> LENGTH: 470
<212> TYPE: DNA

-continued

<213> ORGANISM: Staphylococcus gallinarum
<220> FEATURE:
<223> OTHER INFORMATION: Strain SNUC2913

<400> SEQUENCE: 44
acaggccgtg ttgaacgtgg tcaaatcaaa gtcggtgaag aaatcgaaat catcggtatg 60
caagaagaat caagcaaaac aactgttact ggtgtagaaa tgttccgtaa gttattagac 120
tacgctgaag ctggtgacaa cattggtgca ttattacgtg gtgtttcacg tgaagatgtt 180
caacgtggtc aagttttagc tgctcctggt actattacac cacatacaaa attcaaagcg 240
gaagtttacg ttttatctaa agacgaaggt ggacgtcata ctccattctt cactaactac 300
cgcccacaat tctatttccg tactactgac gtaactggtg ttgttaactt accagaaggt 360
actgaaatgg ttatgcctgg cgataacgtt gaaatggtcg ttgaattaat ttctccaatc 420
gctatcgaag acggtactcg tttctctatc cgtgaaggtg gacgtactgt 470

<210> SEQ ID NO 45
<211> LENGTH: 467
<212> TYPE: DNA
<213> ORGANISM: Staphylococcus haemolyticus
<220> FEATURE:
<223> OTHER INFORMATION: Strain 7067

<400> SEQUENCE: 45
acaggccgtg ttgaacgtgg tcaaatcaaa gttggtgaag aagttgaaat cattggtatc 60
catgacactt ctaaaacaac tgttactggt gtagaaatgt tccgtaaatt attagactac 120
gctgaagctg gtgacaacat cggtgcatta ttacgtggtg ttgctcgtga agacgtacaa 180
cgtggtcaag tattagctgc tccaggttca atcacacctc acacaaaatt caaagcagac 240
gtatacgttt tatctaaaga cgaaggtgga cgtcacactc cattcttcac aaactatcgt 300
ccacaattct atttccgtac tactgacgta actggtgttg ttaacttacc agaaggtaca 360
gaaatggtta tgcctggcga caacgttgaa atgacagtag aattaatcgc tcctatcgcg 420
attgaagacg gtactcgttt ctcaatccgt gaaggtggac gtactgt 467

<210> SEQ ID NO 46
<211> LENGTH: 467
<212> TYPE: DNA
<213> ORGANISM: Staphylococcus haemolyticus
<220> FEATURE:
<223> OTHER INFORMATION: Strain DE0499

<400> SEQUENCE: 46
acaggccgtg ttgaacgtgg tcaaatcaaa gttggtgaag aagttgaaat cattggtatc 60
catgatactt ctaaaacaac tgttactggt gtagaaatgt tccgtaaatt attagactac 120
gctgaagctg gtgacaacat cggtgcatta ttacgtggtg ttgctcgtga agacgtacaa 180
cgtggtcaag tattagctgc tccaggttca atcacaccac acacaaaatt caaagcagac 240
gtatacgttt tatctaaaga cgaaggtgga cgtcacactc cattcttcac aaactatcgt 300
ccacaattct atttccgtac tactgacgta actggtgttg ttaacttacc agaaggtaca 360
gaaatggtta tgcctggcga caacgttgaa atgacagtag aattaatcgc tcctatcgcg 420
attgaagacg gtactcgttt ctcaatccgt gaaggtggac gtactgt 467

<210> SEQ ID NO 47
<211> LENGTH: 467
<212> TYPE: DNA
<213> ORGANISM: Staphylococcus haemolyticus
<220> FEATURE:
<223> OTHER INFORMATION: Strain DE0081

<400> SEQUENCE: 47
acaggccgtg ttgaacgtgg tcaaatcaaa gttggtgaag aagttgaaat cattggtatc 60
catgacactt ctaaaacaac tgttactggt gtagaaatgt tccgtaaatt attagactac 120
gctgaagctg gtgacaacat cggtgcatta ttacgtggtg ttgctcgtga agacgtacaa 180
cgtggtcaag tattagctgc tccaggttca atcacaccac acacaaaatt caaagcagac 240
gtatacgttt tatctaaaga cgaaggtgga cgtcacactc cattcttcac aaactatcgt 300
ccacaattct atttccgtac tactgacgta actggtgttg ttaacttacc agaaggtaca 360
gaaatggtta tgcctggcga caacgttgaa atgacagtag aattaatcgc tcctatcgcg 420
attgaagacg gtactcgttt ctcaatccgt gaaggtggac gtactgt 467

<210> SEQ ID NO 48
<211> LENGTH: 467
<212> TYPE: DNA
<213> ORGANISM: Staphylococcus haemolyticus
<220> FEATURE:
<223> OTHER INFORMATION: Strain SDA2

<400> SEQUENCE: 48
acaggccgtg ttgaacgtgg tcaaatcaaa gttggtgaag aagttgaaat cattggtatc 60
catgacactt ctaaaacaac tgttactggt gtagaaatgt tccgtaaatt attagactac 120
gctgaagctg gtgacaacat cggtgcatta ttacgtggtg ttgctcgtga agacgtacaa 180
cgtggtcaag tattagctgc tccaggttca atcacacctc acacaaaatt taaagcagac 240
gtatacgttt tatctaaaga cgaaggtgga cgtcacactc cattcttcac aaactatcgt 300
ccacaattct atttccgtac tactgacgta actggtgttg ttaacttacc agaaggtaca 360
gaaatggtta tgcctggcga caacgttgaa atgacagtag aattaatcgc tcctatcgcg 420
attgaagacg gtactcgttt ctcaatccgt gaaggtggac gtactgt 467

<210> SEQ ID NO 49
<211> LENGTH: 467
<212> TYPE: DNA
<213> ORGANISM: Staphylococcus haemolyticus
<220> FEATURE:
<223> OTHER INFORMATION: Strain SNUC119

<400> SEQUENCE: 49
acaggccgtg ttgaacgtgg tcaaatcaaa gttggtgaag aagttgaaat cattggtatc 60
catgacactt ctaaaacaac tgttactggt gtagaaatgt tccgtaaatt attagactac 120
gctgaagctg gtgacaacat cggtgcatta ttacgtggtg ttgctcgtga agacgtacaa 180
cgtggtcaag tattagctgc tccaggttca atcacacctc acacaaaatt caaagcagac 240
gtatacgttt tatctaaaga cgaaggtgga cgtcacactc cattcttcac aaactatcgt 300
ccacaattct atttccgtac tactgacgta actggtgttg ttaacttacc agaaggtact 360
gaaatggtta tgcctggcga caacgttgaa atgacagtag aattaatcgc tcctatcgcg 420
attgaagacg gtactcgttt ctcaatccgt gaaggtggac gtactgt 467

<210> SEQ ID NO 50
<211> LENGTH: 467
<212> TYPE: DNA
<213> ORGANISM: Staphylococcus haemolyticus
<220> FEATURE:

<223> OTHER INFORMATION: Strain 7068

<400> SEQUENCE: 50
acaggccgtg ttgaacgtgg tcaaatcaaa gttggtgaag aagttgaaat cattggtatc 60
catgacactt ctaaaacaac tgttactggt gtagaaatgt tccgtaaatt attagactac 120
gctgaagctg gtgacaacat cggtgcatta ttacgtggtg ttgctcgtga agacgtacaa 180
cgtggtcaag tattagctgc tccaggttca atcacacctc acacaaaatt taaagcagac 240
gtatacgttt tatctaaaga cgaaggtgga cgtcacactc cattcttcac aaactatcgt 300
ccacaattct atttccgtac tactgacgta actggtgttg ttaacttacc agaaggtact 360
gaaatggtta tgcctggcga caacgttgaa atgacagtag aattaatcgc tcctatcgcg 420
attgaagacg gtactcgttt ctcaatccgt gaaggtggac gtactgt 467

<210> SEQ ID NO 51
<211> LENGTH: 468
<212> TYPE: DNA
<213> ORGANISM: Staphylococcus hominis
<220> FEATURE:
<223> OTHER INFORMATION: Strain 19A

<400> SEQUENCE: 51
acaggccgtg ttgaacgtgg tcaaatcaaa gttggtgaag aagttgaaat tattggtatc 60
aaagaaactt ctaaaacaac tgttactggt gtagaaatgt tccgtaaatt attagactac 120
gctgaagctg gtgacaacat cggtgcttta ttacgtggtg ttgctcgtga agatgtacaa 180
cgtggtcaag tattagctgc tccaggttca attacacctc acacaaaatt caaagcagac 240
gtatacgttt tatcaaaaga tgaaggtgga cgtcatactc cattcttcac taactatcgt 300
ccacaattct atttccgtac tactgacgta actggtgttg ttaacttacc agaaggtact 360
gaaatggtaa tgcctggcga caacgttgaa atgacaggta gaattaatcg ctcctatcgc 420
gattgaagac ggtactcgtt tctcaatccg tgaaggtgga cgtactgt 468

<210> SEQ ID NO 52
<211> LENGTH: 467
<212> TYPE: DNA
<213> ORGANISM: Staphylococcus hominis
<220> FEATURE:
<223> OTHER INFORMATION: Strain J6

<400> SEQUENCE: 52
acaggccgtg ttgaacgtgg tcaaatcaaa gttggtgaag aagttgaaat tattggtatc 60
aaagaaactt ctaaaacaac tgttactggt gtagaaatgt tccgtaaatt attagactac 120
gctgaagctg gtgacaacat cggtgcttta ttacgtggtg ttgctcgtga agatgtacaa 180
cgtggtcaag tattagctgc tccaggttca attacacctc acacaaaatt caaagcagac 240
gtatacgttt tatcaaaaga tgaaggtgga cgtcatactc cattcttctc taactatcgt 300
ccacaattct atttccgtac tactgacgta actggtgttg ttaacttacc agaaggtact 360
gaaatggtaa tgcctggtga caacgttgaa atgacagtag aattaatcgc tcctatcgcg 420
attgaagacg gtactcgttt ctcaatccgt gaaggtggac gtactgt 467

<210> SEQ ID NO 53
<211> LENGTH: 467
<212> TYPE: DNA
<213> ORGANISM: Staphylococcus hominis
<220> FEATURE:
<223> OTHER INFORMATION: Strain K1

<400> SEQUENCE: 53
acaggccgtg ttgaacgtgg tcaaatcaaa gttggtgaag aagttgaaat tattggtatc 60
aaagaaactt ctaaaacaac tgttactggt gtagaaatgt tccgtaaatt attagactat 120
gctgaagctg gtgacaacat cggtgcttta ttacgtggtg ttgctcgtga agatgtacaa 180
cgtggtcaag tattagctgc tccaggttca attacacctc acacaaaatt caaagcagac 240
gtatacgttt tatcaaaaga tgaaggtggt cgtcatactc cattcttcac taactatcgt 300
ccacaattct atttccgtac tactgacgta actggtgttg ttaacttacc agaaggtact 360
gaaatggtaa tgcctggcga caacgttgaa atgacagtag aattaatcgc tcctatcgcg 420
attgaagacg gtactcgttt ctcaatccgt gaaggtggac gtactgt 467

<210> SEQ ID NO 54
<211> LENGTH: 470
<212> TYPE: DNA
<213> ORGANISM: Staphylococcus hyicus
<220> FEATURE:
<223> OTHER INFORMATION: Strain NCTC7944

<400> SEQUENCE: 54
acaggccgtg ttgaacgtgg tcaaatcaaa gtcggtgaag aagttgaaat catcggtatc 60
actgaagaaa gcaagaaaac aacagttaca ggtgtagaaa tgttccgtaa attattagac 120
tacgctgaag ctggtgacaa catcggtgct ttattacgtg gtgttgcacg tgaagacgta 180
caacgtggac aagtattagc agctcctggc tctattactc cacacacaaa attcaaagct 240
gatgtttacg ttttatctaa agaagaaggt ggacgtcata ctccattctt cactaactac 300
cgcccacaat tctacttccg tactactgac gtaactggcg ttgttcactt accagaaggt 360
actgaaatgg ttatgcctgg cgataacgta gaaatgactg ttgaattgat cgctccaatc 420
gcgattgaag acggtactcg tttctctatc cgtgaaggtg gacgtactgt 470

<210> SEQ ID NO 55
<211> LENGTH: 470
<212> TYPE: DNA
<213> ORGANISM: Staphylococcus intermedius
<220> FEATURE:
<223> OTHER INFORMATION: Strain NCTC11048

<400> SEQUENCE: 55
actggccgtg ttgaacgtgg tcaaatcaaa gttggtgacg aagttgaaat catcggttta 60
actgaagaat cttctaaaac aactgttact ggtgtagaaa tgttccgtaa gttattagac 120
tacgctgaag ctggtgacaa cattggtgct ttattacgtg gtgttgcacg tgaagacatc 180
aaccgtggtc aagtattagc agctcctggt tcaatcacac cacacacaaa atttaaagcg 240
gaagtttacg tattatcaaa agacgaaggt ggacgtcata caccattctt ctctaactac 300
cgcccacaat tctatttccg tactactgac gtaactggtg ttgtaaactt accagaaggt 360
actgaaatgg taatgcctgg cgataacgtt gaaatggaag ttgaattaat ttctccaatc 420
gctatcgaag acggtacacg tttctcaatt cgtgaaggtg gacgtactgt 470

<210> SEQ ID NO 56
<211> LENGTH: 470
<212> TYPE: DNA
<213> ORGANISM: Staphylococcus kloosii
<220> FEATURE:
<223> OTHER INFORMATION: Strain SNUC4696

<400> SEQUENCE: 56
acaggccgtg ttgaacgtgg tcaaatcaaa gtcggtgaag aagttgaaat catcggtatg 60
caagatgaat caagcaaaac aacagttact ggtgtagaaa tgttccgtaa attattagat 120
tacgctgaag ctggtgacaa cattggtgct ttattacgtg gtgttgcacg tgaagacatc 180
caacgtggtc aagttttagc tgctcctggt tcaattacac cacacactaa attcaaagca 240
gaagtttatg tattatcaaa agacgaaggt ggacgtcata ctccattctt cagtaactac 300
cgcccacaat tctatttccg tactactgac gtaacaggtg ttgttacttt accagaaggt 360
actgaaatgg ttatgcctgg tgacaacgtt gaaatggacg ttgaattaat ttcaccaatc 420
gctatcgaag acggtactcg tttctcaatt cgtgaaggtg gccgtactgt 470

<210> SEQ ID NO 57
<211> LENGTH: 467
<212> TYPE: DNA
<213> ORGANISM: Staphylococcus lugdunensis
<220> FEATURE:
<223> OTHER INFORMATION: NCTC12217

<400> SEQUENCE: 57
acaggccgtg ttgaacgtgg tcaaatcaaa gtcggtgaag aagttgaaat tattggtatc 60
cacgatacta ctaaaacaac tgttactggt gtagaaatgt tccgtaaatt attagactac 120
gctgaagctg gtgacaacat cggtgcgtta ttacgtggtg ttgctcgtga agatgtacaa 180
cgtggacaag tattagctgc tccaggttca attacacctc acactaaatt taaagctgac 240
gtatatgttt tatctaaaga tgaaggtgga cgtcatacac cattcttctc aaactaccgc 300
ccacaattct atttccgtac tacagacgta actggtgttg ttaacttacc agaaggtaca 360
gaaatggtta tgcctggcga caacgttgaa atgacagttg aattaatcgc tccaatcgct 420
atcgaagacg gaactcgttt ctcaattcgt gaaggtggac gtactgt 467

<210> SEQ ID NO 58
<211> LENGTH: 467
<212> TYPE: DNA
<213> ORGANISM: Staphylococcus lugdunensis
<220> FEATURE:
<223> OTHER INFORMATION: Strain NCTC12217

<400> SEQUENCE: 58
acaggccgtg ttgaacgtgg tcaaatcaaa gtcggtgaag aagttgaaat tattggtatc 60
cacgatacta ctaaaacaac tgttactggt gtagaaatgt tccgtaaatt attagactac 120
gctgaagctg gtgacaacat cggtgcgtta ttacgtggtg ttgctcgtga agatgtacaa 180
cgtggacaag tattagctgc tccaggttca attacacctc acactaaatt taaagctgac 240
gtatatgttt tatctaaaga tgaaggtgga cgtcatacac cattcttctc aaactaccgc 300
ccacaattct atttccgtac tacagacgta actggtgttg ttaacttacc agaaggtaca 360
gaaatggtta tgcctggcga caacgttgaa atgacagttg aattaatcgc tccaatcgct 420
atcgaagacg gaactcgttt ctcaattcgt gaaggtggac gtactgt 467

<210> SEQ ID NO 59
<211> LENGTH: 467
<212> TYPE: DNA
<213> ORGANISM: Staphylococcus lugdunensis
<220> FEATURE:
<223> OTHER INFORMATION: Strain VISLISI_33

<400> SEQUENCE: 59
acaggccgtg ttgaacgtgg tcaaatcaaa gtcggtgaag aagttgaaat tattggtatc 60
cacgatacta ctaaaacaac ggttactggt gtagaaatgt tccgtaaatt attagactat 120
gctgaagctg gtgacaacat cggtgcgtta ttacgtggtg ttgctcgtga agatgtacaa 180
cgtggacaag tattagctgc tccaggttca attacacctc acactaaatt taaagctgac 240
gtatatgttt tatctaaaga tgaaggtgga cgtcatacac cattcttctc aaactaccgc 300
ccacaattct atttccgtac tacagacgta actggtgttg ttaacttacc agaaggtaca 360
gaaatggtta tgcctggtga caacgttgaa atgacagttg aattaatcgc tccaatcgct 420
atcgaagacg gaactcgttt ctcaattcgt gaaggtggac gtactgt 467

<210> SEQ ID NO 60
<211> LENGTH: 470
<212> TYPE: DNA
<213> ORGANISM: Staphylococcus lutrae
<220> FEATURE:
<223> OTHER INFORMATION: Strain ATCC700373

<400> SEQUENCE: 60
acaggccgtg ttgaacgtgg tcaaatcaaa gttggtgacg aagtagaaat catcggttta 60
actgaagaat cttctaaaac aactgttact ggtgtagaaa tgttccgtaa gttattagac 120
tacgctgaag ctggagacaa cattggtgct ttattacgtg gtgttgcacg tgaagacatc 180
aaccgtggtc aagttttagc agcacctggt tcaatcacac cacatacaaa atttaaagcg 240
gaagtttacg tattatcaaa agacgaaggt ggtcgtcata caccattctt ctctaactac 300
cgcccacaat tctatttccg tacaactgac gtaacaggtg ttgttaattt accagaaggt 360
actgaaatgg taatgcctgg tgacaacgtt gaaatggaag ttgaattaat ttcaccaatc 420
gctatcgaag acggtacacg tttctcaatc cgtgaaggtg gacgtactgt 470

<210> SEQ ID NO 61
<211> LENGTH: 470
<212> TYPE: DNA
<213> ORGANISM: Staphylococcus massiliensis
<220> FEATURE:
<223> OTHER INFORMATION: Strain S46

<400> SEQUENCE: 61
acaggccgtg ttgaacgtgg tcaaatcaaa gtcggtgaag aagttgaaat catcggtctt 60
gctgaagaat caagcaaaac aactgttaca ggtgtagaaa tgttccgtaa gttattagac 120
tacgctgaag ctggtgacaa tatcggtgct ttattacgtg gtgttgcacg tgaagacgtt 180
aaccgtggtc aagtattagc tgctcctggt tcaatcacac ctcacactaa attcaaatca 240
gaagtatacg tattatcaaa agacgaaggt ggtcgtcata caccattctt ctctaactac 300
cgtccacaat tctatttccg tactactgac gtaactggtg ttatccaatt accagaaggt 360
acagaaatgg ttatgcctgg cgataacgtt gaaatggaag ttgaattaat ttctaaaatc 420
gctatcgaag acggtactcg tttctcaatc cgtgaaggtg gacgtactgt 470

<210> SEQ ID NO 62
<211> LENGTH: 470
<212> TYPE: DNA
<213> ORGANISM: Staphylococcus nepalensis
<220> FEATURE:
<223> OTHER INFORMATION: Strain JS9

<400> SEQUENCE: 62

-continued

```
acaggccgtg ttgaacgtgg tcaaatcaaa gtcggtgaag aagttgaaat catcggtatg      60

caagaagaat caagcaaaac aactgttact ggtgtagaaa tgttccgtaa attattagac     120

tatgctgaag ctggtgacaa cattggtgca ttattacgtg gtgttgcacg tgaagatatc     180

caacgtggtc aagttttagc tgctcctggt tcaattacac cgcacacaaa cttcaaagca     240

gaagtttatg tcttatctaa agatgaaggt ggacgtcata cgccattctt cagtaactac     300

cgcccacaat tctatttccg tactactgat gtaactggtg ttgttacttt accagaaggt     360

actgaaatgg ttatgcctgg cgataacgta gaaatgcaag ttgaattgat ttctccaatc     420

gctattgaag acggtactcg tttctcaatc cgtgaaggtg gacgtactgt                470


<210> SEQ ID NO 63
<211> LENGTH: 467
<212> TYPE: DNA
<213> ORGANISM: Staphylococcus pasteuri
<220> FEATURE:
<223> OTHER INFORMATION: Strain JS7

<400> SEQUENCE: 63

acaggccgtg ttgaacgtgg tcaaatcaaa gttggtgaag aagttgaaat catcggttta      60

catgacactt ctaaaacaac tgttactggt gtagaaatgt tccgtaaatt attagactac     120

gctgaagctg gtgacaacat cggtgcatta ttacgtggtg ttgctcgtga agacgtacaa     180

cgtggacaag tattagctgc tccaggttca atcacacctc atacaaaatt caaagcggaa     240

gtttacgttt tatctaaaga tgaaggtgga cgtcatactc cattcttcag taactaccgc     300

ccacaattct atttccgtac tactgacgta actggtgtag ttaacttacc agaaggtact     360

gaaatggtta tgcctggtga caacgttgaa atgacagttg aattaatcgc tccaatcgcg     420

attgaagacg gtactcgttt ctcaatccgt gaaggtggac gtactgt                   467


<210> SEQ ID NO 64
<211> LENGTH: 467
<212> TYPE: DNA
<213> ORGANISM: Staphylococcus pasteuri
<220> FEATURE:
<223> OTHER INFORMATION: Strain 3C

<400> SEQUENCE: 64

acaggccgtg ttgaacgtgg tcaaatcaaa gttggtgaag aagttgaaat catcggttta      60

catgacactt ctaaaacaac tgttactggt gtagaaatgt tccgtaaatt attagactac     120

gctgaagctg gtgacaacat cggtgcatta ttacgtggtg tcgctcgtga agacgtacaa     180

cgtggacaag tattagctgc tccaggttca atcacacctc atacaaaatt caaagcggaa     240

gtttacgttt tatctaaaga tgaaggtgga cgtcatactc cattcttcag taactaccgc     300

ccacaattct atttccgtac tactgacgta actggtgtag ttaacttacc agaaggtact     360

gaaatggtta tgcctggtga caacgttgaa atgacagttg aattaatcgc tccaatcgcg     420

attgaagacg gtactcgttt ctcaatccgt gaaggtggac gtactgt                   467


<210> SEQ ID NO 65
<211> LENGTH: 467
<212> TYPE: DNA
<213> ORGANISM: Staphylococcus petrasii
<220> FEATURE:
<223> OTHER INFORMATION: Strain CCUG62657

<400> SEQUENCE: 65

acaggccgtg ttgaacgtgg tcaaatcaaa gttggtgaag aagttgaaat catcggttta      60
```

cacgacactt ctaaaacaac tgttacaggt gtagaaatgt tccgtaagtt attagactac 120
gctgaagctg gtgacaacat cggtgcttta ttacgtggta tcgctcgtga agacgtacaa 180
cgtggtcaag tattagctgc tccaggttca atcacacctc acactaaatt caaagcagac 240
gtatacgttt tatctaaaga cgaaggtgga cgtcacactc cattcttctc aaactatcgt 300
ccacaattct atttccgtac tactgacgta actggtgttg ttaacttacc agaaggtaca 360
gaaatggtta tgcctggcga caacgttgaa atgacagtag aattaatcgc tcctatcgcg 420
attgaagacg gtactcgttt ctcaatccgt gaaggtggac gtactgt 467

<210> SEQ ID NO 66
<211> LENGTH: 467
<212> TYPE: DNA
<213> ORGANISM: Staphylococcus petrasii
<220> FEATURE:
<223> OTHER INFORMATION: Strain CCM8421

<400> SEQUENCE: 66
acaggccgtg ttgaacgtgg tcaaatcaaa gttggtgaag aagttgaaat tattggtatc 60
catgatactt ctaaaacaac tgttacaggt gtagaaatgt tccgtaaatt attagactac 120
gctgaagctg gtgacaacat cggtgcatta ttacgtggtg ttgctcgtga agacgtacaa 180
cgtggtcaag tattagctgc tccaggttca atcacacctc acactaaatt caaagcagac 240
gtatacgttt tatctaaaga cgaaggtgga cgtcacactc cattcttctc aaactatcgt 300
ccacaattct atttccgtac tactgacgta actggtgttg ttaacttacc agaaggtaca 360
gaaatggtta tgcctggcga caacgttgaa atgacagtag aattaatcgc tcctatcgct 420
attgaagacg gtactcgttt ctcaatccgt gaaggtggac gtactgt 467

<210> SEQ ID NO 67
<211> LENGTH: 470
<212> TYPE: DNA
<213> ORGANISM: Staphylococcus pettenkoferi
<220> FEATURE:
<223> OTHER INFORMATION: Strain FDAARGOS288

<400> SEQUENCE: 67
acaggccgtg ttgaacgtgg tcaaatcaaa gttggtgaag aagttgaaat catcggtatg 60
gctgatgaat cacaaaaaac aactgttact ggtgtagaaa tgttccgtaa gttattagac 120
tacgctgaag ctggtgacaa catcggtgcg ttattacgtg gtattgcacg tgaagacgtt 180
caacgtggtc aagtattagc tgctcctggt tcaatcacac cacacactaa attcaaagct 240
gaagtttacg tattatctaa agacgaaggt ggacgtcaca ctccattctt ctctaactac 300
cgtccacaat tctatttccg tactactgac gtaactggtg tagttaactt accagaaggt 360
acagaaatgg ttatgcctgg tgacaacgtt gaaatggacg ttgaattaat ttcaccaatc 420
gctatcgaag acggtactcg tttctctatc cgtgaaggtg gacgtactgt 470

<210> SEQ ID NO 68
<211> LENGTH: 470
<212> TYPE: DNA
<213> ORGANISM: Staphylococcus piscifermentans
<220> FEATURE:
<223> OTHER INFORMATION: Strain NCTC13836

<400> SEQUENCE: 68
acaggccgtg ttgaacgtgg tcaaatcaaa gtcggtgaag aagttgaaat catcggtatc 60

```
actgaagaaa gcatgaaaac tacagttaca ggtgtagaaa tgttccgtaa attattagac    120

tacgctgaag ctggtgacaa cattggtgct ttattacgtg gtgttgcacg tgaagacgta    180

caacgtggac aagtattagc agctcctggc tctattactc cacacactaa atttaaagct    240

gatgtttacg ttttatctaa agacgaaggt ggacgtcaca ctccattctt ctctaactac    300

cgcccacaat tctacttccg tactactgac gtaacaggcg ttgttaactt accagaaggt    360

actgaaatgg ttatgcctgg cgataacgta gaaatgactg ttgaattgat tgctccaatc    420

gcaatcgaag acggtactcg tttctctatc cgtgaaggtg gacgtactgt               470
```

<210> SEQ ID NO 69
<211> LENGTH: 470
<212> TYPE: DNA
<213> ORGANISM: Staphylococcus pseudintermedius
<220> FEATURE:
<223> OTHER INFORMATION: Strain 53-60

<400> SEQUENCE: 69

```
actggtcgtg ttgaacgtgg tcaaatcaaa gttggtgacg aagtagaaat catcggttta     60

actgaagaat cttctaaaac aactgttact ggtgtagaaa tgttccgtaa gttattagac    120

tacgctgaag ctggtgacaa cattggtgct ttattacgtg gtgttgcacg tgaagacatc    180

aaccgtggtc aagtattagc tgctcctggt tcaatcacac cacacacaaa atttaaagcg    240

gaagtttacg tattatcaaa agacgaaggt ggtcgtcata caccattctt ctctaactac    300

cgcccacaat tctatttccg tactactgac gtaactggtg ttgtaaactt accagaaggt    360

actgaaatgg taatgcctgg cgataacgtt gaaatggaag ttgaattaat ttctccaatc    420

gctatcgaag acggtactcg tttctcaatt cgtgaaggtg gacgtactgt               470
```

<210> SEQ ID NO 70
<211> LENGTH: 470
<212> TYPE: DNA
<213> ORGANISM: Staphylococcus pseudintermedius
<220> FEATURE:
<223> OTHER INFORMATION: Strain 49-44

<400> SEQUENCE: 70

```
actggtcgtg ttgaacgtgg tcaaatcaaa gttggtgacg aagtagaaat catcggttta     60

actgaagaat cttctaaaac aactgttact ggtgtagaaa tgttccgtaa gttattagac    120

tatgctgaag ctggtgacaa cattggtgct ttattacgtg gtgttgcacg tgaagacatc    180

aaccgtggtc aagtattagc tgctcctggt tcaatcacac cacacacaaa atttaaagcg    240

gaagtttacg tattatcaaa agacgaaggt ggtcgtcata caccattctt ctctaactac    300

cgcccacaat tctatttccg tactactgac gtaactggtg ttgtaaactt accagaaggt    360

actgaaatgg taatgcctgg cgataacgtt gaaatggaag ttgaattaat ttctccaatc    420

gctatcgaag acggtactcg tttctcaatt cgtgaaggtg gacgtactgt               470
```

<210> SEQ ID NO 71
<211> LENGTH: 470
<212> TYPE: DNA
<213> ORGANISM: Staphylococcus pseudintermedius
<220> FEATURE:
<223> OTHER INFORMATION: Strain 063228

<400> SEQUENCE: 71

```
actggtcgtg ttgaacgtgg tcaaatcaaa gttggtgacg aagtagaaat catcggttta     60

actgaagaat cttctaaaac aactgttact ggtgtagaaa tgttccgtaa gttattagac    120
```

tacgctgaag ctggtgacaa cattggtgct ttattacgtg gtgttgcacg tgaagacatc 180
aaccgtggtc aagtattagc tgctcctggt tcaatcacac cacacacaaa atttaaagcg 240
gaagtttacg tattatcaaa agacgaaggt ggtcgtcata caccattctt ctctaactac 300
cgcccacaat tctatttccg tactactgac gtaactggtg ttgtaaactt accagaaggt 360
actgaaatgg taatgcctgg cgataacgtt gaaatggaag ttgaattaat ttctccaatc 420
gctattgaag acggtactcg tttctcaatt cgtgaaggtg gacgtactgt 470

<210> SEQ ID NO 72
<211> LENGTH: 470
<212> TYPE: DNA
<213> ORGANISM: Staphylococcus rostri
<220> FEATURE:
<223> OTHER INFORMATION: Strain DSM21968

<400> SEQUENCE: 72
actggccgtg ttgaacgtgg tcaaatcaaa gttggtgaag aagttgaaat catcggttta 60
actgatgaat cagctaaaac aactgttact ggtgtagaaa tgttccgtaa gttattagac 120
tacgctgaag ctggtgacaa cattggtgca ttattacgtg gtgtttcacg tgaagatgta 180
caacgtggtc aagtattagc agctccaggt tctattacac cacacacaaa atttaaagcg 240
gaagtttacg tattatcaaa agacgaaggt ggacgtcaca ctcctttctt ctctaactac 300
cgcccacaat tctatttccg tactactgac gtaactggtg ttgttaactt accagaaggt 360
actgaaatgg ttatgcctgg cgataacgtt gaaatggaag ttgaattaat ttctccaatc 420
gctatcgaag acggtactcg tttctcaatc cgtgaaggtg gacgtactgt 470

<210> SEQ ID NO 73
<211> LENGTH: 467
<212> TYPE: DNA
<213> ORGANISM: Staphylococcus saccharolyticus
<220> FEATURE:
<223> OTHER INFORMATION: Strain 12B0021-3c

<400> SEQUENCE: 73
acaggccgtg ttgaacgtgg tcaaatcaaa gttggtgaag aagttgaaat catcggtatg 60
catgatacaa ctaaaacaac tgttactggt gtagaaatgt tccgtaaatt attagattac 120
gctgaagctg gtgataacat cggtgctcta ttacgtggta ttgcacgtga agacgttcaa 180
cgtgggcaag tattagctgc acctggttca atcacaccac acactaaatt caaagctgaa 240
gtttacgttt tatctaaaga tgaaggtgga cgtcatactc cattcttcag taactatcgt 300
ccacaattct atttccgtac tactgacgta actggtgttg ttaacttacc agaaggcact 360
gaaatggtta tgcctggtga caacgttgaa atgacagttg aattaatcgc tcctattgct 420
atcgaagacg gaactcgttt ctcaattcgt gaaggtggac gtactgt 467

<210> SEQ ID NO 74
<211> LENGTH: 467
<212> TYPE: DNA
<213> ORGANISM: Staphylococcus saccharolyticus
<220> FEATURE:
<223> OTHER INFORMATION: Strain DVP2-17-2406-1c

<400> SEQUENCE: 74
acaggccgtg ttgaacgtgg tcaaatcaaa gttggtgaag aagttgaaat catcggtatg 60
catgatacaa ctaaaacaac tgttactggt gtagaaatgt tccgtaaatt attagattac 120

-continued

```
gctgaagctg gtgataacat cggtgcttta ttacgtggta ttgcacgtga agacgttcaa    180

cgtggtcaag tattagctgc acctggttca atcacaccac acactaaatt caaagctgaa    240

gtttacgttt tatctaaaga tgaaggtgga cgtcatactc cattcttcag taactatcgt    300

ccacaattct atttccgtac tactgacgta actggtgttg ttaacttacc agaaggcact    360

gaaatggtta tgcctggtga caatgttgaa atgacagttg aattaatcgc tcctatcgct    420

atcgaagacg gaactcgttt ctcaattcgt gaaggtggac gtactgt                  467
```

<210> SEQ ID NO 75
<211> LENGTH: 470
<212> TYPE: DNA
<213> ORGANISM: Staphylococcus saprophyticus
<220> FEATURE:
<223> OTHER INFORMATION: Strain 1A

<400> SEQUENCE: 75

```
acaggccgtg ttgaacgtgg tcaaatcaaa gtcggtgaag aaatcgaaat catcggtatg     60

caagaagaat caagcaaaac aactgttact ggtgtagaaa tgttccgtaa attattagac    120

tacgctgaag ctggtgacaa cattggtgca ttattacgtg gtgtttcacg tgatgacgta    180

caacgtggtc aagttttagc tgctcctggt actattacac cacatacaaa attcaaagcg    240

gatgtttacg ttttatctaa agatgaaggt ggtcgtcata caccattctt cactaactac    300

cgcccacaat tctatttccg tactactgac gtaactggtg ttgttaactt accagaaggt    360

actgaaatgg ttatgcctgg tgataacgtt gaaatggatg ttgaattaat ttctccaatc    420

gctattgaag acggtactcg tttctctatc cgtgaaggtg gacgtactgt               470
```

<210> SEQ ID NO 76
<211> LENGTH: 470
<212> TYPE: DNA
<213> ORGANISM: Staphylococcus saprophyticus
<220> FEATURE:
<223> OTHER INFORMATION: Strain FDAARGOS-137

<400> SEQUENCE: 76

```
acaggccgtg ttgaacgtgg tcaaatcaaa gtcggtgaag aaatcgaaat catcggtatg     60

caagaagaat caagcaaaac aactgttact ggtgtagaaa tgttccgtaa attattagac    120

tacgctgaag ctggtgacaa cattggtgca ttattacgtg gtgtttcacg tgatgacgta    180

caacgtggtc aagttttagc tgctcctggt actattacac cacatacaaa attcaaagcg    240

gatgtttacg ttttatctaa agatgaaggt ggtcgtcata caccattctt cactaactac    300

cgcccacaat tctatttccg tactactgac gtaactggtg ttgttaactt accagaaggt    360

actgaaatgg ttatgcctgg cgataacgtt gaaatggatg ttgaattaat ttctccaatc    420

gctattgaag acggtactcg tttctctatc cgtgaaggtg gacgtactgt               470
```

<210> SEQ ID NO 77
<211> LENGTH: 470
<212> TYPE: DNA
<213> ORGANISM: Staphylococcus saprophyticus
<220> FEATURE:
<223> OTHER INFORMATION: Strain ATCC15305

<400> SEQUENCE: 77

```
acaggccgtg ttgaacgtgg tcaaatcaaa gtcggtgaag aaatcgaaat catcggtatg     60

caagaagaat caagcaaaac aactgttact ggtgtagaaa tgttccgtaa attattagac    120

tacgctgaag ctggtgacaa cattggtgca ttattacgtg gtgtttcacg tgatgatgta    180
```

-continued

```
caacgtggtc aagttttagc tgctcctggt actatcacac cacatacaaa attcaaagcg    240

gatgtttacg ttttatctaa agatgaaggt ggtcgtcata cgccattctt cactaactac    300

cgcccacaat tctatttccg tactactgac gtaactggtg ttgttaactt accagaaggt    360

actgaaatgg ttatgcctgg cgataacgtt gaaatggatg ttgaattaat ttctccaatc    420

gctattgaag acggtactcg tttctctatc cgtgaaggtg gacgtactgt              470
```

<210> SEQ ID NO 78
<211> LENGTH: 470
<212> TYPE: DNA
<213> ORGANISM: Staphylococcus schleiferi
<220> FEATURE:
<223> OTHER INFORMATION: Strain OT1-1

<400> SEQUENCE: 78

```
actggtcgtg ttgaacgtgg tcaaatcaaa gttggtgaag aagttgaaat catcggttta     60

gctgaagaat cttctaaaac aactgttact ggtgtagaaa tgttccgtaa attactagac    120

tacgctgaag ctggtgacaa cattggtgct ttattacgtg gtgttgcacg tgaagacatc    180

aaccgtggtc aagtattagc tgctcctggt tcaattacac cacacacaaa gtttaaagca    240

gaagtttacg tattatctaa agacgaaggt ggtcgtcaca ctccattctt ctctaactac    300

cgcccacaat tctatttccg tactactgac gtaactggcg ttgttcactt accagaaggt    360

actgaaatgg ttatgcctgg cgataacgtt gaaatggaag ttgaattaat ttcaccaatc    420

gctatcgaag acggtacgcg tttctcaatt cgtgaaggtg gacgtactgt              470
```

<210> SEQ ID NO 79
<211> LENGTH: 467
<212> TYPE: DNA
<213> ORGANISM: Staphylococcus schweitzeri
<220> FEATURE:
<223> OTHER INFORMATION: >S-schweitzeri-NCTC13712

<400> SEQUENCE: 79

```
acaggccgtg ttgaacgtgg tcaaatcaaa gttggtgaag aagttgaaat catcggttta     60

catgacacat ctaaaacaac tgttacaggt gttgaaatgt tccgtaaatt attagactac    120

gctgaagctg gtgacaacat cggtgcatta ttacgtggtg ttgctcgtga agacgtacaa    180

cgtggtcaag tattagctgc tcctggttca attacaccac atactgaatt caaagcagaa    240

gtttatgtat tatcaaaaga cgaaggtgga cgtcacactc cattcttctc aaactatcgt    300

ccacaattct atttccgtac tactgacgta actggtgttg tacacttacc agaaggtact    360

gaaatggtaa tgcctggtga taacgttgaa atgaaagtag aattaatcgc tcctatcgcg    420

attgaagacg gtactcgttt ctcaatccgt gaaggtggac gtactgt                  467
```

<210> SEQ ID NO 80
<211> LENGTH: 428
<212> TYPE: DNA
<213> ORGANISM: Staphylococcus sciuri
<220> FEATURE:
<223> OTHER INFORMATION: Strain B9-58B

<400> SEQUENCE: 80

```
acaggccgtg ttgaacgtgg tcaaatcact gttggtgaag aagttgaaat catcggttta     60

actgaagaat cttctaaaac aactgtaact ggtgttgaaa tgttccgtaa attattagac    120

ttcgctgaag ctggagataa catcggtgca ttattacgtg gtgttgctcg tgaagacgtt    180
```

-continued aaccgtggtc aagtattagc taaaccaggt tcaatcacac ctcacactaa attcaaagct 240
gaagtttatg tattatctaa agacgaaggt ggacgtcata ctccattctt cacaaactac 300
cgcccacaat tctatttccg tactactgac gtaactggtg tagttaactt accagaaggt 360
actgaaatgg ttatgcctgg cgacaacgtt gaaatggacg ttgaattaat ttcaccaatc 420
gctattga 428

<210> SEQ ID NO 81
<211> LENGTH: 467
<212> TYPE: DNA
<213> ORGANISM: Staphylococcus simiae
<220> FEATURE:
<223> OTHER INFORMATION: Strain NCTC13838

<400> SEQUENCE: 81
acaggccgtg ttgaacgtgg tcaaatcaaa gttggtgaag aagttgaaat catcggatta 60
cacgaaactt ctaaaacaac tgttactggt gtagaaatgt tccgtaaatt attggactac 120
gctgaagctg gtgacaacat tggtgcatta ttacgtggtg ttgctcgtga agacgtacaa 180
cgtggtcaag tattagctgc tcctggttca atcacaccac acactaactt caaagctgaa 240
gtttatgtat tatcaaaaga cgaaggtgga cgtcatactc cattcttctc aaactatcgt 300
ccacaattct atttccgtac tactgacgta actggtgttg ttaatttacc agaaggtact 360
gaaatggtaa tgcctggtga taacgttgaa atgacagtag aattaatcgc tcctatcgcg 420
attgaagacg gtactcgttt ctcaatccgt gaaggtggac gtactgt 467

<210> SEQ ID NO 82
<211> LENGTH: 470
<212> TYPE: DNA
<213> ORGANISM: Staphylococcus simulans
<220> FEATURE:
<223> OTHER INFORMATION: Strain MR1

<400> SEQUENCE: 82
acaggccgtg ttgaacgtgg tcaaatcaaa gtcggtgaag aagttgaaat catcggtatc 60
actgaagaaa gcaagaaaac aacagttaca ggtgtagaaa tgttccgtaa attattagac 120
tacgctgaag ctggtgacaa catcggtgct ttattacgtg gtgttgcacg tgaagacgta 180
caacgtggac aagtattagc agctcctggc tctattactc cacacacaaa attcaaagct 240
gatgtttacg ttttatctaa agaagaaggt ggacgtcata ctccattctt cactaactac 300
cgcccacaat tctacttccg tactactgac gtaactggcg ttgttcactt accagaaggt 360
actgaaatgg ttatgcctgg cgataacgta gaaatgactg ttgaattaat cgctccaatc 420
gcgattgaag acggtactcg tttctctatc cgtgaaggtg gacgtactgt 470

<210> SEQ ID NO 83
<211> LENGTH: 471
<212> TYPE: DNA
<213> ORGANISM: Staphylococcus stepanovicii
<220> FEATURE:
<223> OTHER INFORMATION: Strain NCTC13839

<400> SEQUENCE: 83
actggccgtg ttgaacgtgg acaagttaaa gtcggtgaag aaatcgaaat catcggttta 60
actgaagaat catctaaaac tactgtaact ggtgtagaaa tgttccgtaa attattagac 120
ttcgctgaag ctggagataa tatcggtgca ttattacgtg gtgttgctcg tgaagacgtt 180
aaccgtggtc aagtattagc taaaccaggt tcaatcacac ctcacactaa atttaaagca 240
gaagtttatg tattatctaa agatgaaggt ggacgtcata ctccattctt cactaactac 300
cgcccacaat tctatttccg tactactgac gtaactggtg tagttaactt accagaaggt 360
actgaaatgg ttatgcctgg cgataacgtt gaaatggacg ttgaattaat ttcaccaatc 420
gctattgaag acggtactcg tttctcaatc cgtgaaggtg gacgtacagt t 471

<210> SEQ ID NO 84
<211> LENGTH: 470
<212> TYPE: DNA
<213> ORGANISM: Staphylococcus succinus
<220> FEATURE:
<223> OTHER INFORMATION: Strain 14BME20

<400> SEQUENCE: 84
acaggccgtg ttgaacgtgg tcaaatcaaa gtcggtgaag aaatcgaaat tatcggtatc 60
actgaagaat caagtaaaac aactgttact ggtgtagaaa tgttccgtaa attactagac 120
tacgctgaag ctggtgacaa cattggtgcg ttattacgtg ggtttcacg tgacgatgta 180 caacgtggtc aagttttagc tgctcctggt actattacac cacatacaaa attcaaatct 240
gaagtttacg ttttatcaaa agatgaaggt ggacgtcata ctccattctt cactaactac 300
cgcccacaat tctatttccg tactactgat gtaactggtg ttgtaagttt accagaaggt 360
actgaaatgg ttatgcctgg cgataacgtt gaaatggaag ttgaattaat ctcaccaatc 420
gctattgaag atggtactcg tttctctatc cgtgagggtg gacgtactgt 470

<210> SEQ ID NO 85
<211> LENGTH: 467
<212> TYPE: DNA
<213> ORGANISM: Staphylococcus warneri
<220> FEATURE:
<223> OTHER INFORMATION: Strain 16A

<400> SEQUENCE: 85
acaggccgtg ttgaacgtgg tcaaatcaaa gttggtgaag aagttgaaat catcggttta 60
catgacactt ctaaaacaac tgttactggt gtagaaatgt tccgtaagtt attagactac 120
gctgaagctg gtgacaacat cggtgcttta ttacgtggtg ttgctcgtga agacgtacaa 180
cgtggtcaag tattagctgc tcctggttca attacaccac atacaaaatt caaagcggaa 240
gtttacgttt tatctaaaga cgaaggtgga cgtcacactc cattcttcag taactaccgc 300
ccacaattct atttccgtac tactgacgta actggcgttg ttcaattacc agaaggtact 360
gaaatggtta tgcctggtga taacgttgaa atgacagtag aattaatcgc tcctatcgcg 420
attgaagacg gtactcgttt ctcaatccgt gaaggtggac gtactgt 467

<210> SEQ ID NO 86
<211> LENGTH: 470
<212> TYPE: DNA
<213> ORGANISM: Staphylococcus xylosus
<220> FEATURE:
<223> OTHER INFORMATION: Strain S170

<400> SEQUENCE: 86
acaggccgtg ttgaacgtgg tcaaatcaaa gtcggtgaag aaatcgaaat catcggtatg 60
caagaagagt caagcaaaac aacagttact ggtgtagaaa tgttccgtaa attattagac 120
tacgctgaag ctggtgacaa cattggtgca ttattacgtg gtgtttcacg tgatgatatc 180
caacgtggtc aagttttagc tgctcctggt actattacac cacatactaa attcaaagct 240

-continued

```
gacgtttatg ttttatcaaa agatgaaggt ggtcgtcata caccattctt cactaactac    300

cgcccacaat tctatttccg tactactgac gtaacaggtg ttgttacttt accagaaggt    360

actgaaatgg ttatgcctgg cgataacgta gaaatgaacg ttgaattgat ttctccaatc    420

gctattgaag acggtactcg tttctctatc cgtgaaggtg gacgtactgt               470
```

<210> SEQ ID NO 87
<211> LENGTH: 470
<212> TYPE: DNA
<213> ORGANISM: Staphylococcus xylosus
<220> FEATURE:
<223> OTHER INFORMATION: Strain 2

<400> SEQUENCE: 87

```
acaggccgtg ttgaacgtgg tcaaatcaaa gtcggtgaag aaatcgaaat cattggtatg     60

caagaagagt caagcaaaac aacagttact ggtgtagaaa tgttccgtaa attattagac    120

tacgctgaag ctggtgacaa cattggtgca ttattacgtg gtgtttcacg tgatgacatc    180

caacgtggtc aagttttagc tgctcctggt actattacac cacatactaa attcaaagct    240

gacgtttatg ttttatcaaa agatgaaggt ggtcgtcata caccattctt cactaactac    300

cgcccacaat tctatttccg tactactgac gtaacaggtg ttgttacttt accagaaggt    360

actgaaatgg ttatgcctgg cgataacgta gaaatgaacg ttgaattgat ttctccaatc    420

gctattgaag acggtactcg tttctctatc cgtgaaggtg gacgtactgt               470
```

<210> SEQ ID NO 88
<211> LENGTH: 467
<212> TYPE: DNA
<213> ORGANISM: Staphylococcus epidermidis
<220> FEATURE:
<223> OTHER INFORMATION: Strain N1

<400> SEQUENCE: 88

```
acaggccgtg ttgaacgtgg tcaaatcaaa gttggtgaag aagttgaaat catcggtatg     60

cacgaaactt ctaaaacaac tgttactggt gtagaaatgt tccgtaaatt attagactac    120

gctgaagctg gtgacaacat cggtgcttta ttacgtggtg ttgcacgtga agacgtacaa    180

cgtggtcaag tattagctgc tcctggttct attacaccac acacaaaatt caaagctgaa    240

gtatacgtat tatctaaaga tgaaggtgga cgtcacactc cattcttcac taactatcgc    300

ccacaattct atttccgtac tactgacgta actggtgttg taaacttacc agaaggtaca    360

gaaatggtta tgcctggcga caacgttgaa atgacagttg aattaatcgc tccaatcgct    420

attgaagacg gaactcgttt ctcaattcgt gaaggtggac gtactgt                  467
```

<210> SEQ ID NO 89
<211> LENGTH: 467
<212> TYPE: DNA
<213> ORGANISM: Staphylococcus epidermidis
<220> FEATURE:
<223> OTHER INFORMATION: Strain N2

<400> SEQUENCE: 89

```
acaggccgtg ttgaacgtgg tcaaatcaaa gttggtgaag aagttgaaat catcggtatg     60

catgaaactt ctaaaacaac tgttactggt gtagaaatgt tccgtaaatt attagactac    120

gctgaagctg gtgacaacat cggtgcttta ttacgtggtg ttgcacgtga agacgtacaa    180

cgtggtcaag tattagctgc tcctggttct attacaccac acacaaaatt caaagctgaa    240

gtatacgtat tatctaaaga tgaaggtgga cgtcacactc cattcttcac taactatcgc    300
```

-continued

```
ccacaattct atttccgtac tactgacgta actggtgttg taaacttacc agaaggtaca    360

gaaatggtta tgcctggcga caacgttgaa atgacagttg aattaatcgc tccaatcgct    420

atcgaagacg gaactcgttt ctcaattcgt gaaggtggac gtactgt                  467
```

<210> SEQ ID NO 90
<211> LENGTH: 467
<212> TYPE: DNA
<213> ORGANISM: Staphylococcus epidermidis
<220> FEATURE:
<223> OTHER INFORMATION: Strain N3

<400> SEQUENCE: 90

```
acaggccgtg ttgaacgtgg tcaaatcaaa gttggtgaag aagttgaaat catcggtatg     60

cacgaaactt ctaaaacaac tgttactggt gtagaaatgt tccgtaaatt attagactac    120

gctgaagctg gtgacaacat cggtgcttta ttacgtggtg ttgcacgtga agacgtacaa    180

cgtggtcaag tattagctgc tcctggttct attacaccac acacaaaatt caaagctgaa    240

gtatacgtat tatctaaaga tgaaggtgga cgtcacactc cattcttcac taactatcgc    300

ccacaattct atttccgtac tactgacgta actggtgttg taaacctacc agaaggtaca    360

gaaatggtta tgcctggcga caacgttgaa atgacagttg aattaatcgc tccaatcgct    420

atcgaagacg gaactcgttt ctcaattcgt gaaggtggac gtactgt                  467
```

<210> SEQ ID NO 91
<211> LENGTH: 467
<212> TYPE: DNA
<213> ORGANISM: Staphylococcus capitis
<220> FEATURE:
<223> OTHER INFORMATION: Strain N1

<400> SEQUENCE: 91

```
acaggccgtg ttgaacgtgg tcaaatcaaa gttggtgaag aagttgaaat catcggtatc     60

cacgaaactt ctaaaacaac tgttactggt gtagaaatgt tccgtaaatt attagactac    120

gctgaagctg gtgacaacat cggtgcttta ttacgtggtg ttgctcgtga agacgtacaa    180

cgtggtcaag tattagctgc tcctggttca atcacaccac acactaaatt caaagcggaa    240

gtttacgttt tatctaaaga cgaaggtgga cgtcacactc cattcttcag taactaccga    300

ccacaattct atttccgtac tactgacgta actggtgttg ttaacttacc agaaggtact    360

gaaatggtta tgcctggcga caacgttgaa atgacagttg aattaatcgc tcctatcgct    420

attgaagacg gtactcgttt ctcaatccgt gaaggtggac gtactgt                  467
```

<210> SEQ ID NO 92
<211> LENGTH: 467
<212> TYPE: DNA
<213> ORGANISM: Staphylococcus haemolyticus
<220> FEATURE:
<223> OTHER INFORMATION: Strain N1

<400> SEQUENCE: 92

```
acaggccgtg ttgaacgtgg tcaaatcaaa gttggtgaag aagttgaaat cattggtatc     60

catgacactt ctaaaacaac tgttactggt gtagaaatgt tccgtaaatt attagactac    120

gctgaagctg gtgacaacat tggtgcatta ttacgtggtg ttgctcgtga agacgtacaa    180

cgtggtcaag tattagctgc tccaggttca atcacacctc acacaaaatt taaagcagac    240

gtatacgttt tatctaaaga cgaaggtgga cgtcacactc cattcttcac aaactatcgt    300
```

```
ccacaattct atttccgtac tactgacgta actggtgttg ttaacttacc agaaggtaca    360

gaaatggtta tgcctggtga caacgttgaa atgacagtag aattaatcgc tcctatcgcg    420

attgaagacg gtactcgttt ctcaatccgt gaaggtggac gtactgt                  467


<210> SEQ ID NO 93
<211> LENGTH: 467
<212> TYPE: DNA
<213> ORGANISM: Staphylococcus hominis
<220> FEATURE:
<223> OTHER INFORMATION: Strain N1

<400> SEQUENCE: 93

acaggccgtg ttgaacgtgg tcaaatcaaa gttggtgaag aagttgaaat tattggtatc     60

aaagaaactt ctaaaacaac tgttactggt gtagaaatgt tccgtaaatt attagactac    120

gctgaagctg gtgacaacat cggtgcttta ttacgtggtg ttgctcgtga agatgtacaa    180

cgtggtcaag tattagctgc tccaggttca attacacctc acacaaaatt caaagcagac    240

gtatacgttt tatcaaaaga tgaaggtgga cgtcatactc cattcttcac taactatcgt    300

ccacaattct atttccgtac tactgacgta actggtgttg ttaacttacc agaaggtact    360

gaaatggtaa tgcctggcga caacgttgaa atgacagtag aattaatcgc tcctatcgcg    420

attgaagacg gtactcgttt ctcaatccgt gaaggtggac gtactgt                  467


<210> SEQ ID NO 94
<211> LENGTH: 467
<212> TYPE: DNA
<213> ORGANISM: Staphylococcus hominis
<220> FEATURE:
<223> OTHER INFORMATION: Strain N2

<400> SEQUENCE: 94

acaggccgtg ttgaacgtgg tcaaatcaaa gttggtgaag aagttgaaat tattggtatc     60

aaagaaactt ctaaaacaac tgttactggt gtagaaatgt tccgtaaatt attagactac    120

gctgaagctg gtgacaacat cggtgcttta ttacgtggtg ttgctcgtga agatgtacaa    180

cgtggtcaag tattagctgc tccaggttca attacacctc acacaaaatt caaagcagac    240

gtatacgttt tatcaaaaga tgaaggtgga cgtcatactc cattcttcac taactatcgt    300

ccacaattct atttccgtac tactgacgta actggtgttg ttaacttacc agaaggtact    360

gaaatggtaa tgcctggcga taacgttgaa atgacagtag aattaatcgc tcctatcgcg    420

attgaagacg gtactcgttt ctcaatccgt gaaggtggac gtactgt                  467


<210> SEQ ID NO 95
<211> LENGTH: 467
<212> TYPE: DNA
<213> ORGANISM: Staphylococcus hominis
<220> FEATURE:
<223> OTHER INFORMATION: Strain N3

<400> SEQUENCE: 95

acaggccgtg ttgaacgtgg tcaaatcaaa gttggtgaag aagttgaaat tattggtatc     60

aaagaaactt ctaaaacaac tgttactggt gtagaaatgt tccgcaaatt attagactac    120

gctgaagctg gtgacaacat cggtgcttta ttacgtggtg ttgctcgtga agatgtacaa    180

cgtggtcaag tattagctgc tccaggttca attacacctc acacaaaatt caaagcagac    240

gtatacgttt tatcaaaaga tgaaggtgga cgtcatactc cattcttcac taactatcgt    300

ccacaattct atttccgtac tactgacgta actggtgttg ttaacttacc agaaggtact    360
```

gaaatggtaa tgcctggcga taacgttgaa atgacagtag aattaatcgc tcctatcgcg 420
attgaagacg gtactcgttt ctcaatccgt gaaggtggac gtactgt 467

<210> SEQ ID NO 96
<211> LENGTH: 467
<212> TYPE: DNA
<213> ORGANISM: Staphylococcus hominis
<220> FEATURE:
<223> OTHER INFORMATION: Strain N4

<400> SEQUENCE: 96
acaggccgtg ttgaacgtgg tcaaatcaaa gttggtgaag aagttgaaat tattggtatc 60
aaagaaactt ctaaaacaac tgttactggt gtagaaatgt tccgtaaatt attagactac 120
gctgaagctg gtgacaacat cggtgcttta ttacgtggtg ttgctcgtga agatgtacaa 180
cgtggtcaag tattagctgc tccaggttca attacacctc acacaaaatt caaagcagac 240
gtatacgttt tatcaaaaga tgaaggtggt cgtcatactc cattcttcac taactatcgt 300
ccacaattct atttccgtac tactgacgta actggtgttg ttaacttacc agaaggtact 360
gaaatggtaa tgcctggcga caacgttgaa atgacagtag aattaatcgc tcctatcgcg 420
attgaagacg gtactcgttt ctcaatccgt gaaggtggac gtactgt 467

<210> SEQ ID NO 97
<211> LENGTH: 467
<212> TYPE: DNA
<213> ORGANISM: Staphylococcus hominis
<220> FEATURE:
<223> OTHER INFORMATION: Strain N5

<400> SEQUENCE: 97
acaggccgtg ttgaacgtgg tcaaatcaaa gttggtgaag aagttgaaat tattggtatc 60
aaagaaactt ctaaaacaac tgttactggt gtagaaatgt tccgtaaatt attagactac 120
gctgaagctg gtgacaacat cggtgcttta ttacgtggtg ttgctcgtga agatgtacaa 180
cgtggtcaag tattagctgc tccaggttca attacacctc acacaaaatt caaagcagac 240
gtatatgttt tatcaaaaga tgaaggtgga cgtcatactc cattcttcac taactatcgt 300
ccacaattct atttccgtac tactgacgta actggtgttg ttaacttacc agaaggtact 360
gaaatggtaa tgcctggcga caacgttgaa atgacagtag aattaatcgc tcctatcgcg 420
attgaagacg gtactcgttt ctcaatccgt gaaggtggac gtactgt 467

<210> SEQ ID NO 98
<211> LENGTH: 467
<212> TYPE: DNA
<213> ORGANISM: Staphylococcus warneri
<220> FEATURE:
<223> OTHER INFORMATION: Strain N1

<400> SEQUENCE: 98
acaggccgtg ttgaacgtgg tcaaatcaaa gttggtgaag aagttgaaat catcggttta 60
catgacactt ctaaaacaac tgttactggt gtagaaatgt tccgtaagtt attagactac 120
gctgaagctg gtgacaacat cggtgcttta ttacgtggtg ttgctcgtga agacgtacaa 180
cgtggtcaag tattagctgc tcctggttca attacaccac atacaaaatt caaagcggaa 240
gtttacgttt tatctaaaga cgaaggtgga cgtcacactc cattcttcag taactaccgc 300
ccacaattct atttccgtac tactgacgta actggcgttg ttcaattacc agaaggtact 360
gaaatggtta tgcctggtga caacgttgaa atgacagtag aattaatcgc tcctatcgcg 420
attgaagacg gtactcgttt ctcaatccgt gaaggtggac gtactgt 467

<210> SEQ ID NO 99
<211> LENGTH: 467
<212> TYPE: DNA
<213> ORGANISM: Staphylococcus warneri
<220> FEATURE:
<223> OTHER INFORMATION: Strain N2

<400> SEQUENCE: 99
acaggccgtg ttgaacgtgg tcaaatcaaa gttggtgaag aagttgaaat catcggttta 60
catgacactt ctaaaacaac tgttactggt gtagaaatgt tccgtaagtt attagactac 120
gctgaagctg gtgacaacat cggtgcttta ttacgtggtg ttgctcgtga agacgtacaa 180
cgtggtcaag tattagctgc tcctggttca attacaccac atacaaaatt caaagcggaa 240
gtttacgttt tatctaaaga cgaaggtgga cgtcacactc cattcttcag taactaccgc 300
ccgcaattct atttccgtac tactgacgta actggcgttg ttcaattacc agaaggtact 360
gaaatggtta tgcctggtga caacgttgaa atgacagtag aattaatcgc tcctatcgcg 420
attgaagacg gtactcgttt ctcaatccgt gaaggtggac gtactgt 467

<210> SEQ ID NO 100
<211> LENGTH: 467
<212> TYPE: DNA
<213> ORGANISM: Staphylococcus warneri
<220> FEATURE:
<223> OTHER INFORMATION: Strain N3

<400> SEQUENCE: 100
acaggccgtg ttgaacgtgg tcaaatcaaa gttggtgaag aagttgaaat cattggttta 60
catgacactt ctaaaacaac tgttactggt gtagaaatgt tccgtaagtt attagactac 120
gctgaagctg gtgacaacat cggtgcttta ttacgtggtg ttgctcgtga agacgtacaa 180
cgtggtcaag tattagctgc tcctggttca attacaccac atacaaaatt caaagcggaa 240
gtttacgttt tatctaaaga cgaaggtgga cgtcacactc cattcttcag taactaccgc 300
ccacaattct atttccgtac tactgacgta actggcgttg ttcaattacc agaaggtact 360
gaaatggtta tgcctggtga caacgttgaa atgacagtag aattaatcgc tcctatcgcg 420
attgaagacg gtactcgttt ctcaatccgt gaaggtggac gtactgt 467

<210> SEQ ID NO 101
<211> LENGTH: 19
<212> TYPE: DNA
<213> ORGANISM: Artificial Sequence
<220> FEATURE:
<223> OTHER INFORMATION: rpsk forward primer

<400> SEQUENCE: 101
tggcacgtaa acaagtatc 19

<210> SEQ ID NO 102
<211> LENGTH: 18
<212> TYPE: DNA
<213> ORGANISM: Artificial Sequence
<220> FEATURE:
<223> OTHER INFORMATION: rpsk reverse primer

<400> SEQUENCE: 102
gacgacgttt tggtggac 18

-continued

```
<210> SEQ ID NO 103
<211> LENGTH: 24
<212> TYPE: DNA
<213> ORGANISM: Artificial Sequence
<220> FEATURE:
<223> OTHER INFORMATION: tuf-alt forward primer

<400> SEQUENCE: 103

ggccgtgttg aacgtggtca aatc                                   24


<210> SEQ ID NO 104
<211> LENGTH: 25
<212> TYPE: DNA
<213> ORGANISM: Artificial Sequence
<220> FEATURE:
<223> OTHER INFORMATION: tuf-alt reverse primer
<220> FEATURE:
<221> NAME/KEY: modified_base
<222> LOCATION: 2
<223> OTHER INFORMATION: /mod_base="OTHER"
      /note="n = i"

<400> SEQUENCE: 104

tnaccatttc agtaccttct ggtaa                                  25
```